(12) United States Patent
Nambu

(10) Patent No.: US 8,989,473 B2
(45) Date of Patent: Mar. 24, 2015

(54) MEDICAL IMAGING APPARATUS AND MEDICAL IMAGE DIAGNOSIS APPARATUS

(75) Inventor: Kyojiro Nambu, Nasushiobara (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 328 days.

(21) Appl. No.: 13/515,642

(22) PCT Filed: Jul. 1, 2011

(86) PCT No.: PCT/JP2011/003772
§ 371 (c)(1),
(2), (4) Date: Jun. 13, 2012

(87) PCT Pub. No.: WO2012/004956
PCT Pub. Date: Jan. 12, 2012

(65) Prior Publication Data
US 2012/0250973 A1    Oct. 4, 2012

(30) Foreign Application Priority Data
Jul. 5, 2010    (JP) ................... 2010-152793

(51) Int. Cl.
G06K 9/00 (2006.01)
A61B 6/12 (2006.01)
A61B 6/00 (2006.01)

(52) U.S. Cl.
CPC . *A61B 6/12* (2013.01); *A61B 6/469* (2013.01); *A61B 6/487* (2013.01)
USPC ........................................ 382/132

(58) Field of Classification Search
None
See application file for complete search history.

(56) References Cited

U.S. PATENT DOCUMENTS

| 6,144,754 | A | 11/2000 | Okano et al. |
| 6,229,907 | B1 | 5/2001 | Okano et al. |
| 6,747,674 | B1 | 6/2004 | Asami |
| 2004/0007180 | A1 | 1/2004 | Yamasaki et al. |
| 2005/0259116 | A1 | 11/2005 | Araoka |
| 2008/0118131 | A1 | 5/2008 | Skinner et al. |
| 2008/0306766 | A1 | 12/2008 | Ozeki et al. |
| 2009/0022400 | A1 | 1/2009 | Matsuzaki |

(Continued)

FOREIGN PATENT DOCUMENTS

| CN | 1643933 A | 7/2005 |
| CN | 1648808 A | 8/2005 |

(Continued)

OTHER PUBLICATIONS

International Search Report Issued Sep. 27, 2011 in PCT/JP11/03772 Filed Jul. 1, 2011.

(Continued)

*Primary Examiner* — Bhavesh Mehta
*Assistant Examiner* — Andrew Moyer
(74) *Attorney, Agent, or Firm* — Oblon, McClelland, Maier & Neustadt, L.L.P.

(57) ABSTRACT

An X-ray diagnosis apparatus displays X-ray moving images by irradiating a subject with X-rays and detecting X-rays that have penetrated the subject, and includes a selection mechanism and a display. The selection mechanism selects images of high importance from among the X-ray moving images based on working-state information related to the working state of the operator performing surgery on the subject. The display list displays the selected images as thumbnails.

20 Claims, 22 Drawing Sheets

(56) References Cited

U.S. PATENT DOCUMENTS

| | | | |
|---|---|---|---|
| 2009/0207316 A1* | 8/2009 | Cupal et al. | 348/700 |
| 2010/0070523 A1* | 3/2010 | Delgo et al. | 707/769 |
| 2010/0097392 A1* | 4/2010 | Nishiyama et al. | 345/593 |

FOREIGN PATENT DOCUMENTS

| | | |
|---|---|---|
| CN | 1702645 A | 11/2005 |
| CN | 101754713 A | 6/2010 |
| JP | 7 143968 | 6/1995 |
| JP | 8 275195 | 10/1996 |
| JP | 10 262953 | 10/1998 |
| JP | 10-308899 A | 11/1998 |
| JP | 2001 149354 | 6/2001 |
| JP | 2002 95640 | 4/2002 |
| JP | 2003 338952 | 11/2003 |
| JP | 2004 91917 | 3/2004 |
| JP | 2005 270328 | 10/2005 |
| JP | 2006 6915 | 1/2006 |
| JP | 2006-20874 A | 1/2006 |
| JP | 2008 126070 | 6/2008 |
| JP | 2008 301984 | 12/2008 |
| JP | 2009 183335 | 8/2009 |
| JP | 2009 240559 | 10/2009 |
| JP | 2010 5326 | 1/2010 |
| WO | 2009 013940 | 1/2009 |

OTHER PUBLICATIONS

Combined Chinese Office Action and Search Report issued Sep. 18, 2013, in Patent Application No. 201180002858.6.

* cited by examiner

MEDICAL IMAGING APPARATUS AND MEDICAL IMAGE DIAGNOSIS APPARATUS

CROSS-REFERENCE TO RELATED APPLICATION

This application is based upon and claims the benefit of priority from Japanese Patent Application No. 2010-152793, filed Jul. 5, 2010; the entire contents of which are incorporated herein by reference.

FIELD

Embodiments of the present invention relate to a medical imaging apparatus and medical image diagnosis apparatus that, based on an X-ray fluoroscopic examination in which a subject is irradiated with X-rays and X-rays that have penetrated the subject are detected, display X-ray image group acquired in chronological order.

BACKGROUND

In recent years, due to advantages such as low invasiveness in relation to the subject, there has been a significant increase in techniques performed by inserting a funicular insert instrument configured by a narrow, funicular member into the body. These insert instruments include catheters as well as guide wires that are introduced together with catheters, etc. In this specification, these and other funicular insert instruments are hereinafter referred to as "wire(s)". Because wires generally absorb more X-rays than the human body, in X-ray images, they are observed as relatively clear black, narrow lines.

One example of the X-ray fluoroscopic examination in which wires are used is catheterization under X-ray fluoroscopy. In catheterization under X-ray fluoroscopy, a catheter is inserted into the body from an artery of the femoral region, etc., and the catheter is guided to the affected area while referring to X-ray fluoroscopy images (moving image) displayed in real time to perform treatment.

A medical imaging apparatus used in catheterization under X-ray fluoroscopy irradiates X-rays for fluoroscopy to a subject into whom a catheter has been inserted, detects X-rays that have penetrated the subject, and based on the detection results, forms and displays X-ray fluoroscopy images depicting the interior of the subject. Moreover, the medical imaging apparatus is configured to be able to change fluoroscopy conditions, including the X-ray dosage during fluoroscopy of the subject, based on information from input operations, and when the X-ray dosage is raised, finer X-ray fluoroscopy images is displayed as a result. In finer X-ray fluoroscopy images, it is possible to make the tissues inside the subject, including the blood vessels, easier to view (e.g., Patent Document 1).

Moreover, to display a finer X-ray fluoroscopy image, it is possible to occasionally supply a contrast agent from the catheter and observe the image of the contrast agent that appears for only a few seconds to confirm the position to which the guide wire should be advanced.

As a result of such an X-ray fluoroscopic examination, a series of moving images is obtained. If these moving images are kept as they are, it is difficult to subsequently find a desired examination from among examination records related to many patients. Therefore, conventionally, a method has been used to automatically or manually select a single appropriate frame from among the moving images obtained in the X-ray fluoroscopic examination and use this image as a representative image of the examination. This image is referred to as a thumbnail.

Even if the desired examination is found using a conventional thumbnail, it also takes time to find the desired shot from within the examination. Moreover, it is common to perform procedures, etc. for multiple purposes during a single examination, but in such cases, it is not possible to sufficiently represent the characteristics of the examination in a single thumbnail.

Methods of generating multiple thumbnails from among the moving images include a method of simultaneously playing back and viewing all channels of footage sampled over only several seconds every few minutes. In this way, it is possible to broadly recognize the type of surgery performed, the arrangement of equipment and staff, and when the equipment, etc. was operated.

Then, when finding an important scene or a shot representing a turning point, a cue is manually attached, and later, by selecting the cue, the frame corresponding to the time can be accessed.

For example, in the moving images, prolonged continuations of great changes in the footage occur when the surgery has been discontinued for some reason and people are moving around, or when the surgery proceeds to the next process and the layout of equipment and staff is being adjusted, etc. By attaching a cue to such time periods and sampling the preceding and proceeding frames, it becomes easy to infer what stage the surgery is in.

Similar techniques include a technique in which a designation of an operator is received, bookmark data is generated at any timing on the timescale of the moving images, and the frames are associated with the bookmark data and recorded (e.g., Patent Document 2).

DETAILED DESCRIPTION

Figure 1:
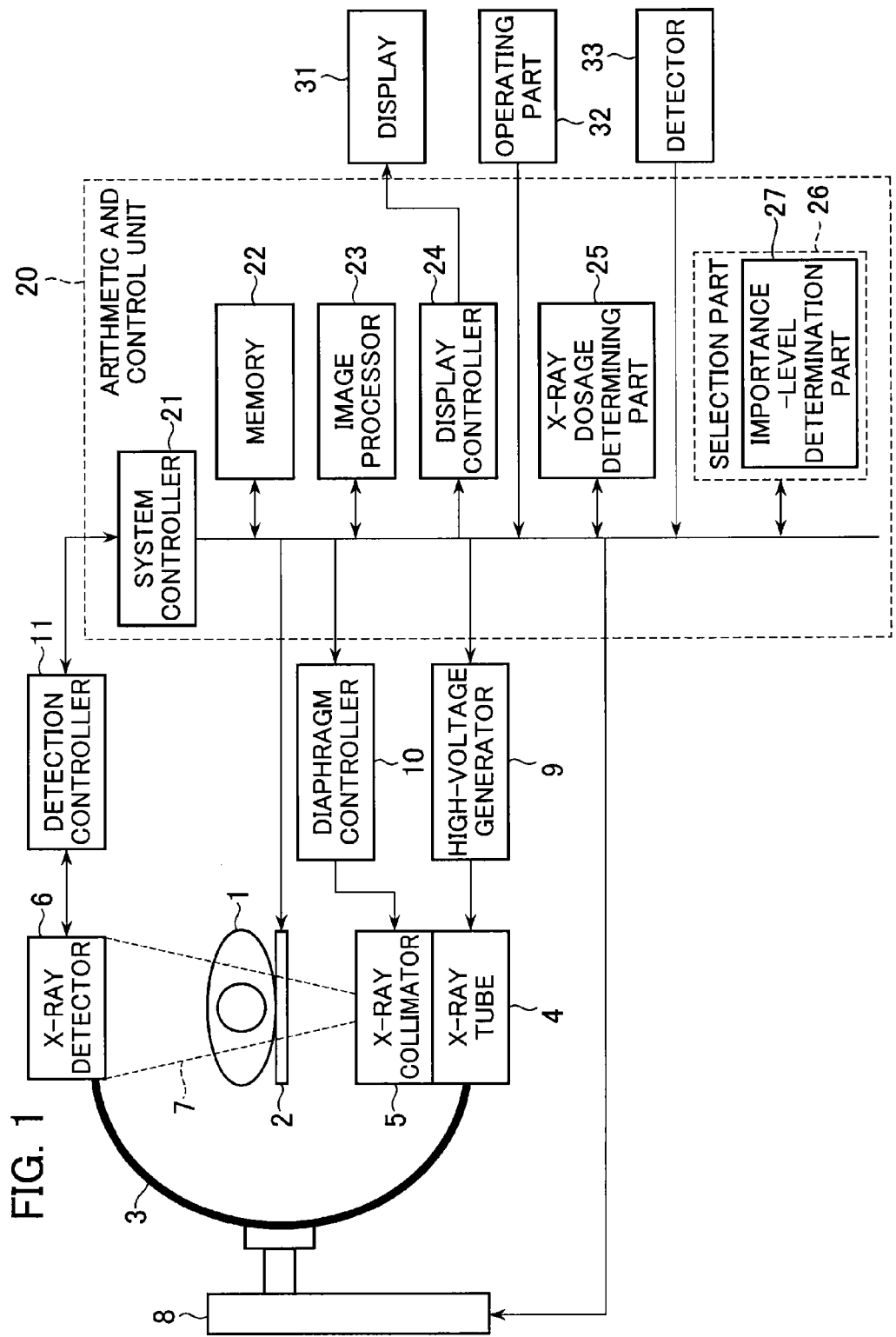
FIG. 1 is an image showing the overall configuration of a medical imaging apparatus according to a first embodiment.

A medical imaging apparatus according to an embodiment displays X-ray moving images by irradiating a subject with X-rays and detecting X-rays that have penetrated the subject, and includes a selection means and a display means. The selection means selects images of high importance from among the x-ray moving images based on working-state information related to the working state of the operator performing surgery on the subject. The display means list displays the selected images as thumbnails.

Moreover, a medical imaging apparatus according to another embodiment displays X-ray moving images by irradiating a subject with X-rays and detecting X-rays that have penetrated the subject, and includes an importance-level determination means, a selection means, and a display means. The importance-level determination means determines the importance level of image in the X-ray moving images. The selection means selects images from among the X-ray moving images based on the importance level determined by the importance-level determination means. The display means list displays the selected images as thumbnails.

Furthermore, a medical image diagnosis apparatus according to an embodiment captures moving images related to a subject, and includes a selection means and a display means. The selection means selects images of high importance from among the moving images. The display means list displays the selected images as thumbnails.

An example of an embodiment of a medical imaging apparatus will now be described in detail with reference to the drawings.

The medical imaging apparatus according to the present embodiment is used in surgeries performed by inserting a wire into the body of a subject. The following is a particularly detailed description of cases applied to catheterization under X-ray fluoroscopy. This medical imaging apparatus automatically selects appropriate X-ray images from among the X-ray image group acquired chronologically through catheterization under X-ray fluoroscopy, and list displays them as thumbnails. By displaying them in a list, it becomes easy to find desired examination records and to determine the location within the examination records where desired footage has been recorded.

In the present embodiment, unless specified otherwise, "images" are not distinguished from "image data". The image data processed by the medical imaging apparatus is generally paint data (also referred to as raster data or bitmap data, etc.). Paint data is formed by elements such as pixels and voxels, etc., and are image data formed by assigning values (pixel values) to each element. An image is a representation of the image data that is observable using a prescribed computer program. In this way, image data and images practically correspond to one another on a one-to-one basis.

When automatically selecting appropriate X-ray images from within the X-ray image group, this is performed based on data representing the working state of the operator during catheterization under X-ray fluoroscopy. The X-ray images may be selected based on the data themselves, or the importance levels of the X-ray images may be obtained based on the data to select the X-ray images based on the importance levels. In the following description, unless specified otherwise, the "working state of the operator" refers to the working states of staff including the operator. Moreover, unless specified otherwise, "movement by the operator" refers to movement by the staff including the operator.

The following is a detailed description of the manner in which data representing the working state of the operator are acquired, and the manner in which the importance levels of X-ray images are obtained based on the data. First, the working state of the operator may refer to the following. A first working state is the state of manipulation of an instrument (wire) by the operator, such as a state in which the instrument is manipulated by the operator, for example. A second working state is the posture of the operator when they are looking at a display for displaying X-ray fluoroscopy images, for example. A third working state is biological information of the operator when the respiration of the operator is restrained or when the operator is in a state of tension during operations to insert the apical part of a wire, which requires very minute operations from the operator. A fourth working state is actions of the operator, such as when the operator engages in conversation. A fifth working state is when the operator or an X-ray technician, etc. performs an operation to instruct the apparatus to reduce or increase the dosage, or to stop or restart irradiation. A combination of one or any two of the above first through fifth working states of the operator is used as information for making a determination when obtaining the importance levels of the X-ray images.

This medical imaging apparatus obtains the importance levels of X-ray images based on this information for making a determination. The following are detailed descriptions of which of the above first through fifth working states of the operator to detect as information for making a determination, the method of detection, judgment standards that act as a baseline for comparing the detected results, and the details of determinations, with reference to various embodiments.

First Embodiment

A first embodiment will be described. First, the configuration of a medical imaging apparatus for performing catheterization under X-ray fluoroscopy will be described. Next, an example will be described in which the amount of change in the shape of a wire is detected as the result of detecting the manipulated state of the wire handled by the operator during catheterization under X-ray fluoroscopy. Then, an example will be described in which the importance levels of X-ray images acquired during catheterization under X-ray fluoroscopy are obtained based on the detection results.

[Device Configuration]

The configuration of the medical imaging apparatus according to the present embodiment will be described. An example configuration of this medical imaging apparatus (X-ray diagnosis apparatus) is shown in FIG. 1. This medical imaging apparatus has a mechanical composition similar to that of conventional examples.

The subject 1 represents the patient undergoing catheterization under X-ray fluoroscopy. The subject 1 is placed on a top board 2. The top board 2 is part of a bed device that is not shown in the diagrams. The bed device is provided with a drive mechanism for moving the top board 2. In the present embodiment, the subject 1 is placed on the top board 2 by lying down. Some medical imaging apparatuses are provided with a standing loading table that supports the subject in an upright state, but in catheterization under X-ray fluoroscopy, treatment is normally performed for a subject supported in a supine state on the top board.

A C-arm 3 is a support member formed roughly in the shape of the letter C. An X-ray tube 4 and an X-ray collimator 5 are supported on one end of the C-arm 3, and an X-ray detector 6 is supported on the other end. As a result, the X-ray tube 4 and X-ray collimator 5, and the X-ray detector 6 are arranged at positions facing each other across the subject 1.

The C-arm 3 is movably supported by the drive mechanism 8. By moving the C-arm 3 under the control of an arithmetic and control unit 20, the drive mechanism 8 changes the positions and tilt angles of the X-ray tube 4, the X-ray collimator 5, and the X-ray detector 6.

The X-ray tube 4 generates X-rays 7 when a high voltage is applied from a high-voltage generator 9. The X-ray collimator 5 includes aperture blades that regulate the irradiation range (solid angle and cross-sectional shape) of the X-rays 7 generated from the X-ray tube 4. A diaphragm controller 10 moves the position of the aperture blades to change the irradiation range of the X-rays 7. Operations of the high-voltage generator 9 and the diaphragm controller 10 are controlled by the arithmetic and control unit 20.

The X-rays 7 with an irradiation range regulated by the X-ray collimator 5 are irradiated on the subject 1. The X-rays 7 that have penetrated the subject 1 are projected to the X-ray detector 6. The X-ray detector 6 detects the X-rays 7, converts the detection results into electrical signals, and transmits them to a detection controller 11. The detection controller 11 transmits these electrical signals to the arithmetic and control unit 20. Moreover, the detection controller 11 controls operations of the X-ray detector 6.

The X-ray detector 6 may be configured using, for example, a Flat Panel Detector (FPD) or an Image Intensifier (I.I.).

In the present embodiment, the X-ray tube 4 is controlled to irradiate pulse X-rays 7 at a prescribed time interval. This time interval is set to, for example, around $\frac{1}{30}$ to $\frac{1}{5}$ of a second (irradiation count per second of 5 to 30). Although irradiation at a maximum count of several tens per second, for example, is possible with the medical imaging apparatus, this level of time interval is selected to reduce the X-ray exposure of the subject 1 and the operator. As a result, moving images at a frame rate of around 5 to 30 frames per second are obtained. It is also possible to continuously irradiate X-rays instead of repeatedly irradiating pulse X-rays in this manner.

The arithmetic and control unit 20 controls each part of the X-ray imaging device and executes various arithmetic processes. The arithmetic and control unit 20 has a configuration similar to that of, for example, a common computer. As an example, the arithmetic and control unit 20 is configured by including a microprocessor, a storage device (RAM, ROM, hard disk, etc.), and a communication interface, etc. An operating device, an input device and a display device are connected to the arithmetic and control unit 20.

The system controller 21 in the arithmetic and control unit 20 controls each part of the medical imaging apparatus. Examples include the following: controlling the drive mechanism 8 to move the C-arm 3; controlling the high-voltage generator 9 to change the X-ray conditions (dosage of the X-rays 7, frame rate, etc.) and perform, for example, upward and downward adjustments of the X-ray dosage as described below; controlling the diaphragm controller 10 to change the irradiation range of the X-rays 7; and controlling the detection controller 11 to cause it to control the operations of the X-ray detector 6. Moreover, the system controller 21 controls each part of the arithmetic and control unit 20.

An image processor 23 forms an image (digital image data) of the subject 1 based on electrical signals transmitted from the X-ray detector 6 via the detection controller 11. Moreover, the image processor 23 performs various image processes for this image. The details of the image processor 23 will be described below.

A display controller 24 receives control from the system controller 21 and displays information on a display 31. The display 31 is configured by using a display device such as a Liquid Crystal Display (LCD) or a CRT (Cathode Ray Tube), etc.

Based on the detection results output from operator-movement detectors ("detectors") 33, an X-ray dosage determining part 25 determines whether to reduce the current X-ray dosage, and if it makes a determination to reduce the current X-ray dosage, it outputs a control signal to reduce the X-ray dosage. Based on the control signal output from the X-ray dosage determination part 25, the system controller 21 controls the high-voltage generator 9 to cause it to change the X-ray conditions (X-ray dosage, etc.), and performs upward and downward adjustments of the X-ray dosage, for example. Details of the X-ray dosage determination part 25 will be described below. Furthermore, the system controller 21 performs upward and downward adjustments of the X-ray dosage based on other control signals (e.g., instruction signals from an operating part 32) as well.

A selection part 26 includes an importance-level determination part 27 that determines the importance levels of X-ray images included in the X-ray image group based on the detection results of the detector 33. Furthermore, the selection part 26 selects one or multiple X-ray images based on the determined importance levels. Details on the manner in which the importance-level determination part 27 determines the importance levels, and the manner in which the selection part 26 selects X-ray images based on the importance levels will be described below. Here, the selection part 26 is an example of the "selection means" of the present invention. Moreover, the importance-level determination part 27 is an example of the "importance-level determination means" of the present invention.

The operating part 32 is used for operating the medical imaging apparatus or for information input, etc. The operating part 32 is configured by including operating devices and input devices such as a keyboard, a mouse, a control panel, and a pedal operating part, etc. The pedal operating part outputs instruction signals for initiating or stopping X-ray irradiation, and outputs instruction signals for increasing or decreasing the X-ray dosage.

The detector 33 detects the amount of change in the shape of a wire based on the difference between a wire image in any one frame from among multiple frames included in the moving images and a wire image in a frame from further in the past, and outputs the detection results. Details of the detector 33 will be described below.

[Image Processor]

Figure 2:
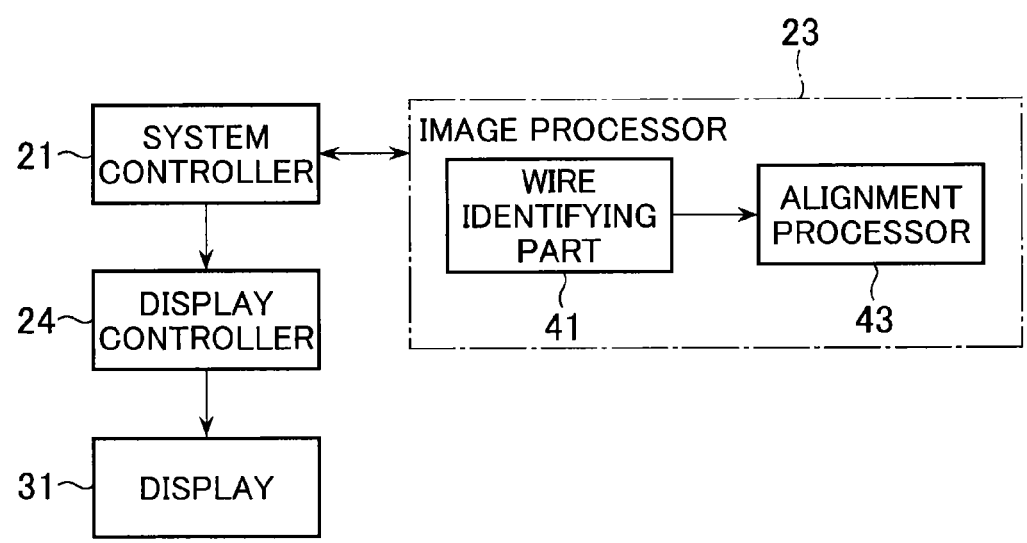
FIG. 2 is a block diagram showing the configuration of the control system of the medical imaging apparatus shown in FIG. 1.

An example configuration of the image processor 23 will be described with further reference to FIG. 2. The image processor 23 is provided with a wire identifying part 41 and an alignment processor 43.

The image processor 23 executes the processes described below in real time. Real-time processes in the present embodiment refer to responding to the input of electrical signals (corresponding to one frame) from the X-ray detector 6 into the arithmetic and control unit 20 by immediately executing a process on the frame and outputting (displaying) the results. As a result, it becomes possible to display the status of the wire as a moving image within a delay time that is considered to have no delay in practice.

(Wire Identifying Part)

As described above, in the present embodiment, moving images with a frame rate of approximately 5 to 30 frames per second are obtained. The wire identifying part identifies the image of the guide wire in each of the multiple frames configuring this moving image.

Here, a frame refers to each of a series of still images configuring the moving image. Moreover, the above multiple frames are not necessarily all of the frames configuring the moving image. For example, they may be multiple frames determined according to a start timing and an end timing of characteristic functions of the present embodiment (described below). Furthermore, during surgery, moving images of around several to 30 frames are continuously generated every second over a long period of time (for example, several hours), but the functions according to the present embodiment may be used for several minutes from this period, for example. The image processor 23 initiates operations when there is an instruction to initiate use of the functions according to the present invention, and executes processes such as the following. The frames subject to the processes of the image processor 23 are the series of frames acquired after the time of the instruction to initiate use.

Figure 3:
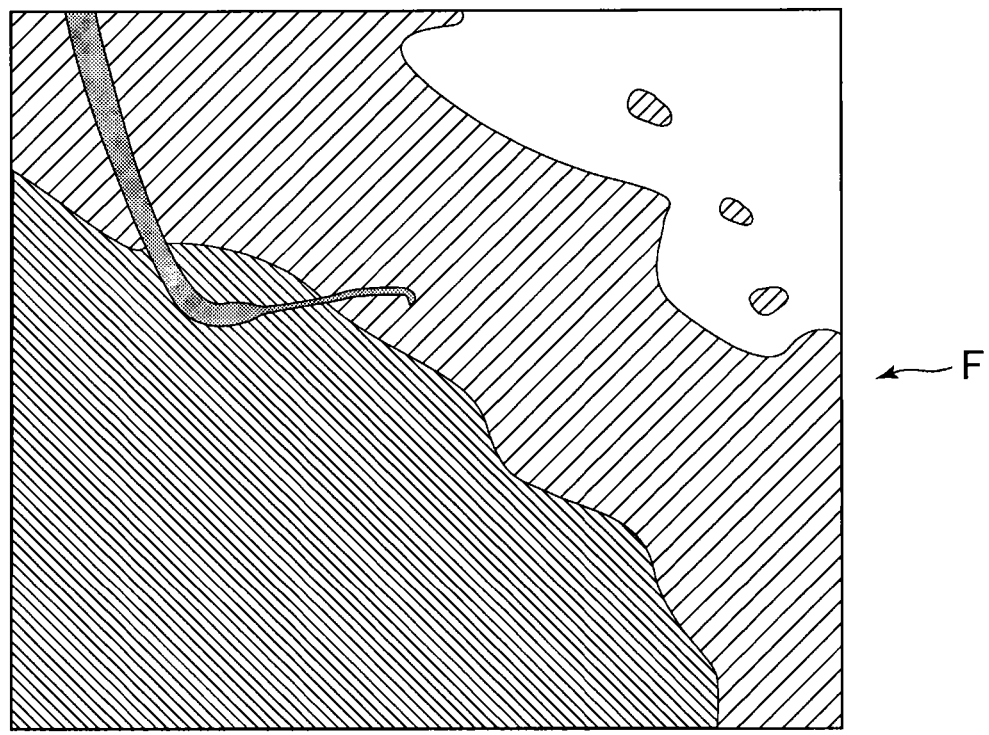
FIG. 3 is a drawing showing a frame that is displayed by the medical imaging apparatus shown in FIG. 1 and depicts a wire inserted into a body

The operations of the wire identifying part 41 will be described in more detail. An example of a frame is shown in FIG. 3. Frame F shows a catheter and a guide wire inserted from the femoral artery into the coronary artery via the aorta. Generally, in an X-ray image, areas with low amounts of X-ray penetration are often depicted as black, and areas with high amounts are often depicted as white. FIG. 3 also conforms to this display method. A schematic diagram of the image shown in FIG. 3 is shown in FIG. 4.

The image C' that appears as a dim strip in the frame F is the shadow of a catheter. Moreover, the image C that appears slightly black at the position of the apical portion of the image C' of the catheter is the shadow of a guide wire. The tip of the catheter has an opening. The tip side of the guide wire is projected from this opening. Moreover, the large curvature near the center of the guide wire has occurred because the catheter has become embedded in the bifurcation from the aorta to the coronary artery. Looking at the apical portion of the image C of the guide wire, although it is slight, there is a large curvature. This is a bend that is preliminarily placed on the guide wire to make it easier to insert the guide wire into bifurcations, etc. of blood vessels. The frame F depicts this type of state.

Figure 4:
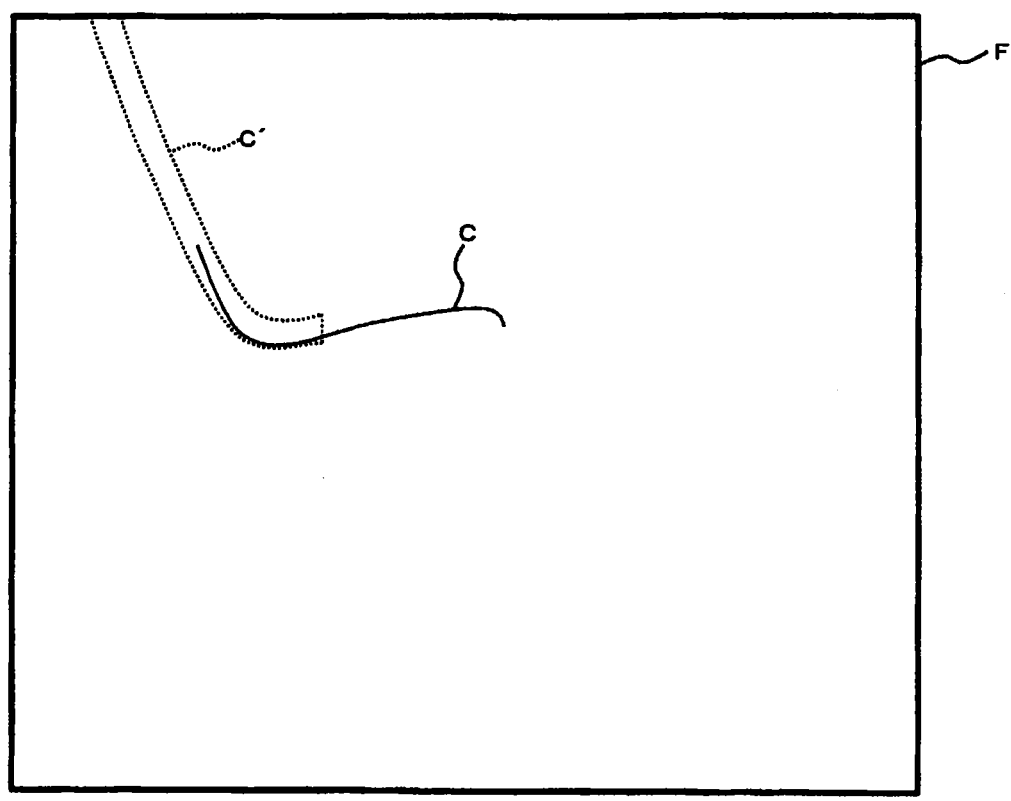
FIG. 4 is a drawing showing an outline of the frame shown in FIG. 3.

It should be noted that, in FIG. 4, images depicting body tissues such as blood vessels, organs and bones, etc. are omitted to facilitate easy viewing (the same applies to other schematic diagrams). In the actual frames, complex gradation patterns corresponding to body tissues are also depicted, as shown in FIG. 3. Moreover, in the present embodiment, unless specified otherwise, images are not distinguished from their actual objects (catheter, guide wire, body tissues, etc.).

In the present embodiment, frames such as that shown in FIG. 3 are processed. In order to more easily and highly accurately identify the wire image C, first, the wire identifying part 41 performs a highlighting process to make the image C clearer. As an example of this highlighting process, there is a method of performing non-linear brightness conversion to decrease density irregularities of the wire image C, and then performing an image filtering process that extracts components with high spatial frequencies from among the various spatial-frequency components of the image. This image filtering process eliminates global, smooth gradations and leaves only local, minute variation components.

The highlighting process is not limited to the example described above. For example, it is possible to determine the details of the highlighting process appropriately in accordance with the characteristics of the medical imaging apparatus being used or the subject. Moreover, it is possible to realize the highlighting process by appropriately combining known image processing technology.

The wire identifying part 41 performs an appropriate pattern extraction process on the frame F and identifies the wire image C. For this pattern extraction process, it is possible to appropriately use any image processing technique, such as a threshold process on pixel values or a spatial filtering process. Moreover, the identification of the wire image C may be configured to identify the contour of the image C instead of identifying the entirety of the image C.

Mathematically, the wire is a smooth curve (three-dimensional curve) embedded in a real space (three-dimensional space). On the other hand, images obtained by the medical imaging apparatus are two-dimensional curves in which this three-dimensional curve is projected on a planar surface. This projection uses the position of the X-ray tube 4 (i.e., the position at which the X-rays 7 are generated) as the viewpoint, and uses the detector plane of the X-ray detector 6 as a projected planar surface. Consequently, it is possible to capture the identified wire image C as a two-dimensional curve (also represented by the symbol "C").

Figure 5:
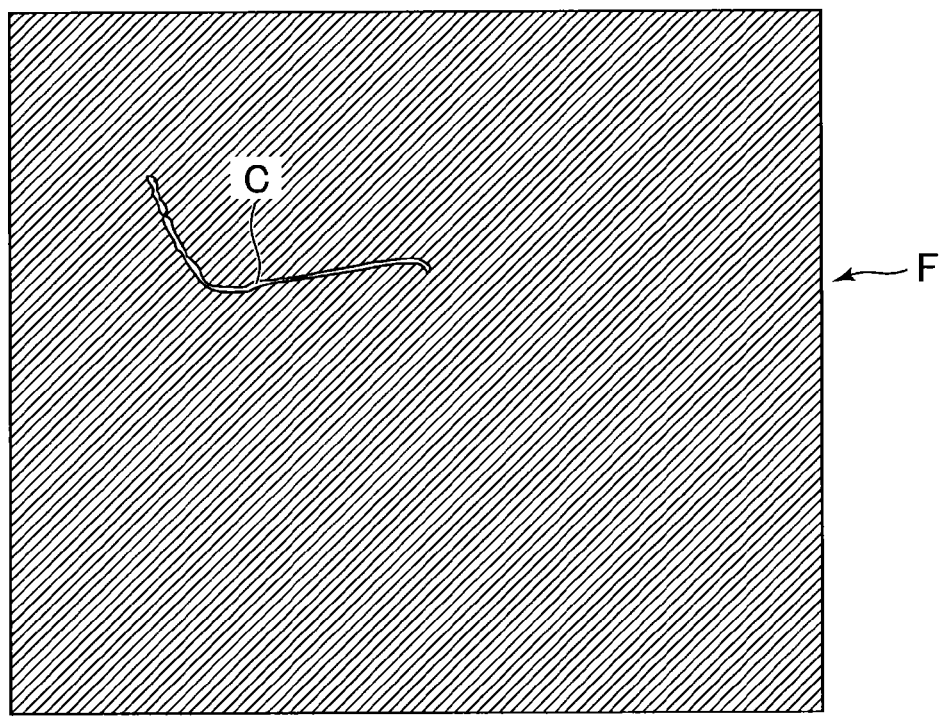
FIG. 5 is a drawing showing a wire image extracted from the frame shown in FIG. 3.
Figure 6:
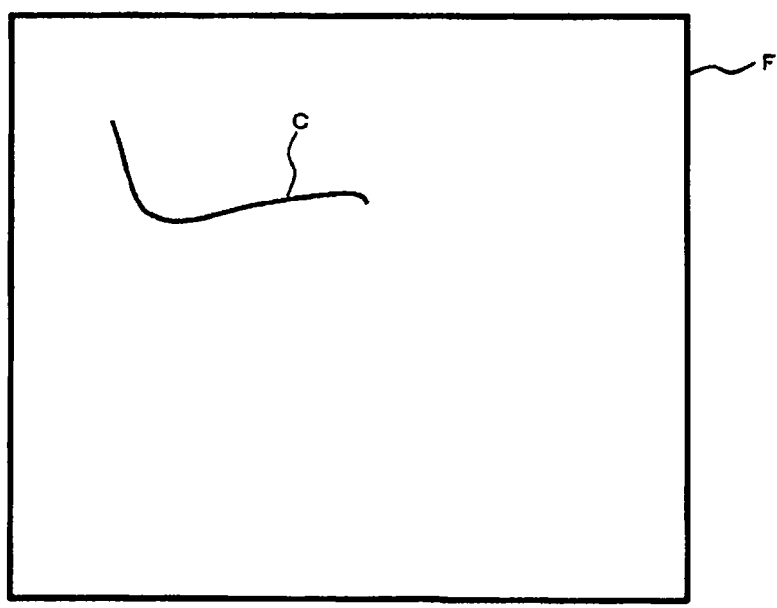
FIG. 6 is a drawing showing a two-dimensional curve based on the wire image shown in FIG. 5.

The wire identifying part 41 extracts the image C of the identified wire from the frame F. The alignment processor 43 represents the extracted image C as a two-dimensional curve (described later). An example of the extracted wire image C is shown in FIG. 5. Moreover, an example of a two-dimensional curve C based on the wire image C is shown in FIG. 6.

For each frame based on the electrical signals transmitted sequentially from the X-ray detector 6 at the time interval described above, the wire identifying part 41 executes the above processes in real time. As a result, multiple wire images are obtained in chronological order.

Figure 7:
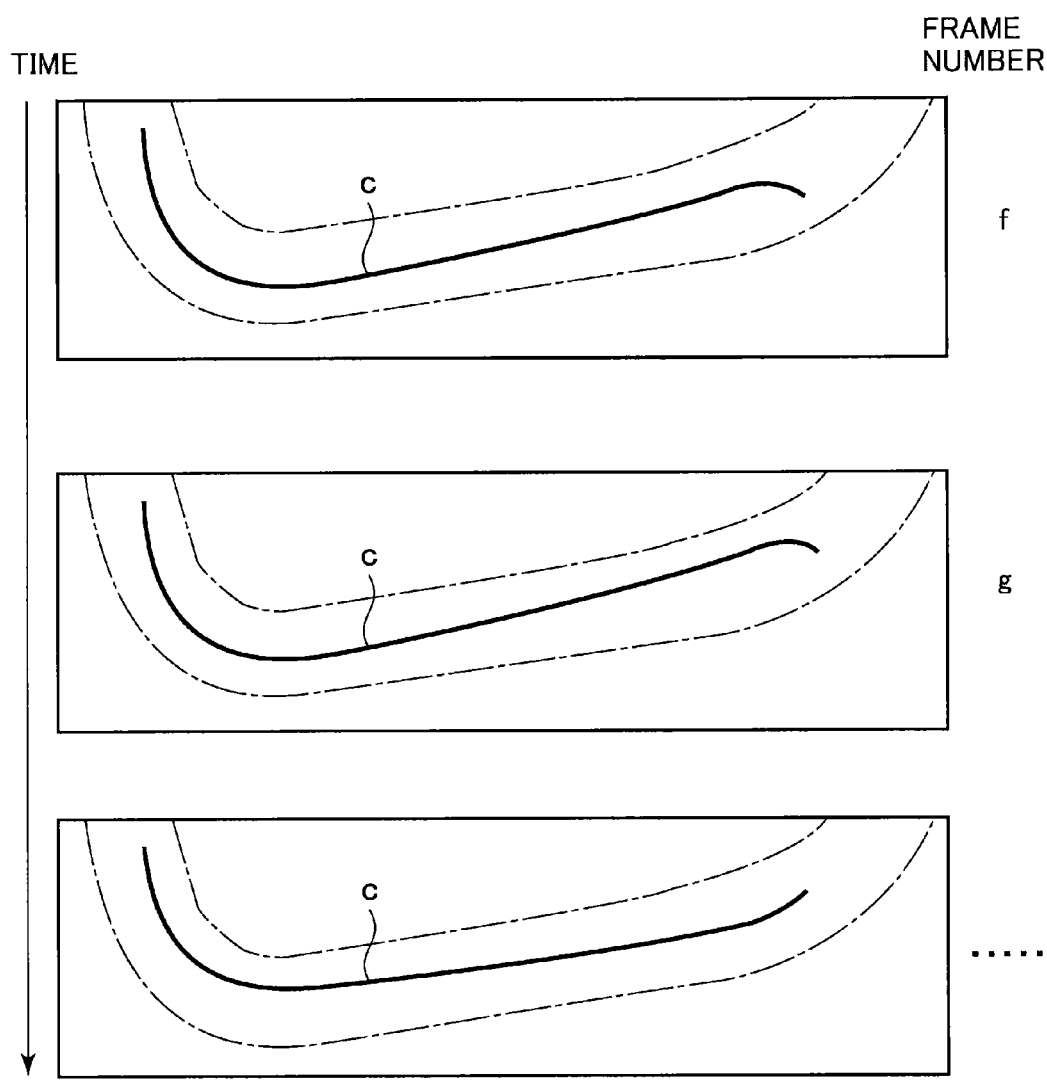
FIG. 7 is a drawing showing two-dimensional curves based on multiple wire images obtained chronologically by the medical imaging apparatus shown in FIG. 1.
Figure 8:
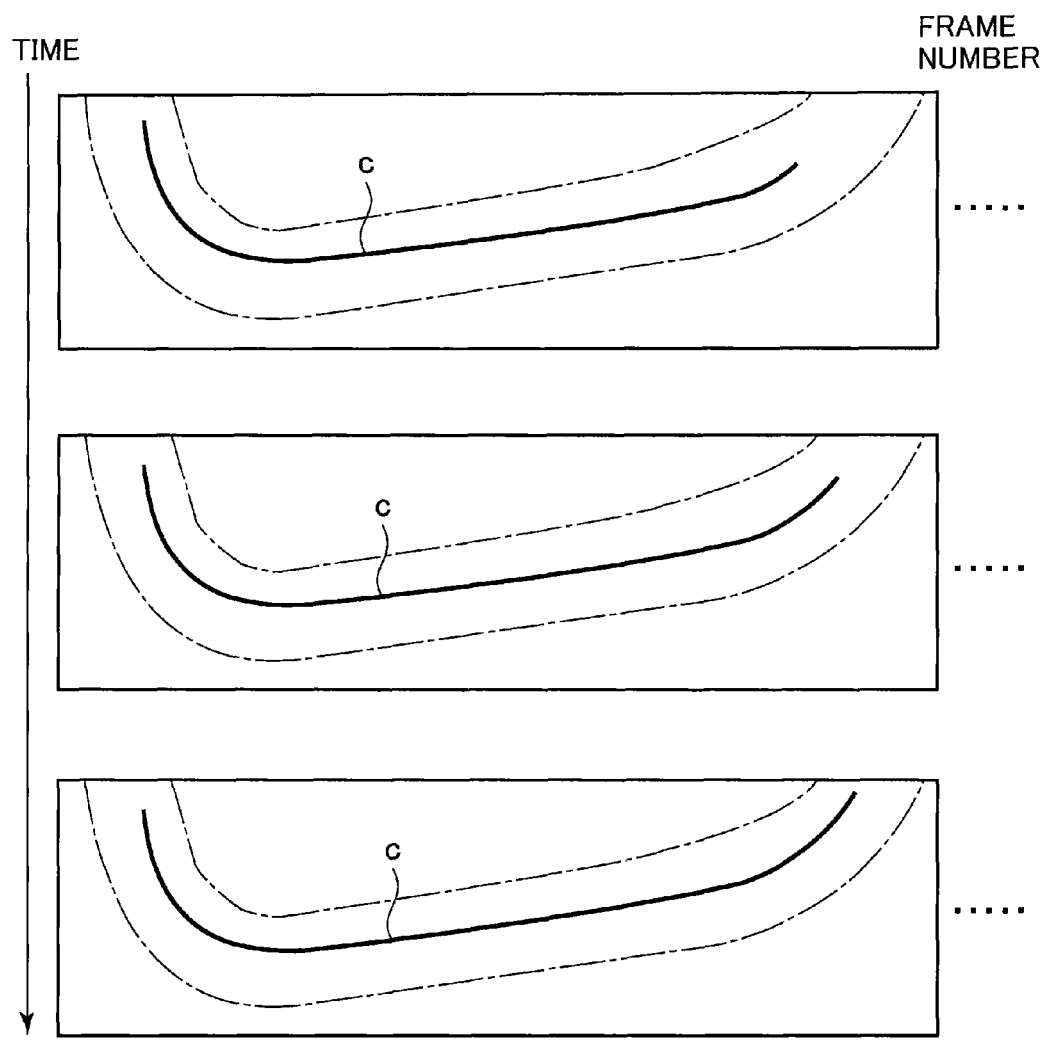
FIG. 8 is a drawing showing two-dimensional curves based on multiple wire images obtained chronologically by the medical imaging apparatus shown in FIG. 1.

FIG. 7 shows the two-dimensional curve C based on the wire image extracted from each of a group of temporally continuous frames in a case in which the wire has been axially rotated by a wire manipulation by the operator. Moreover, FIG. 8 shows the two-dimensional curve C based on the wire image extracted from each of a group of temporally continuous frames in a case in which the wire has been advanced by a wire manipulation by the operator. The gradual changes in the position and shape of the two-dimensional curve C are the result of movement caused by motion generated by the respiration and heartbeat, etc. of the subject 1, and of changes in shape of the wire itself caused by movement of the wire in the blood vessel.

When observing a wire inside a body, it is desirable to irradiate X-rays from a direction that is as perpendicular to the wire as possible. This is because doing so makes motion of the wire easiest to observe in the footage (i.e., in the moving images). When comparing the wire images C between two temporally adjacent frames, differences between the two are minute changes in shape or length, and although changes in the shape and position of the wire occur due to parallel displacement and rotational transfer caused by movements of the subject 1, their respective shapes are similar.

Furthermore, the apical portion of the wire may undergo drastic changes in shape due to manipulations to twist the wire or due to impact with the blood vessel wall. However, other portions reflect the shape of the blood vessel at the position where the wire is currently passing, and almost never undergo drastic changes in shape. In the present embodiment, the following processes are executed by using this fact.

(Alignment Processor)

The alignment processor 43 executes processes such as the following for each frame other than the first frame from among the series of frames subject to the application of the functions according to the present embodiment. Here, the first frame is referred to as a standard for position in processes for subsequent frames. The alignment processor 43 aligns the frame with a past frame so that the wire image C of the frame best overlaps the wire image C of the past frame. The alignment process for frames is described in detail below.

First, the alignment processor 43 obtains the two-dimensional curve C representing the shape of the wire image C in each frame (refer to FIG. 6). Here, image processes such as a thinning process is performed as needed.

Figure 9A:
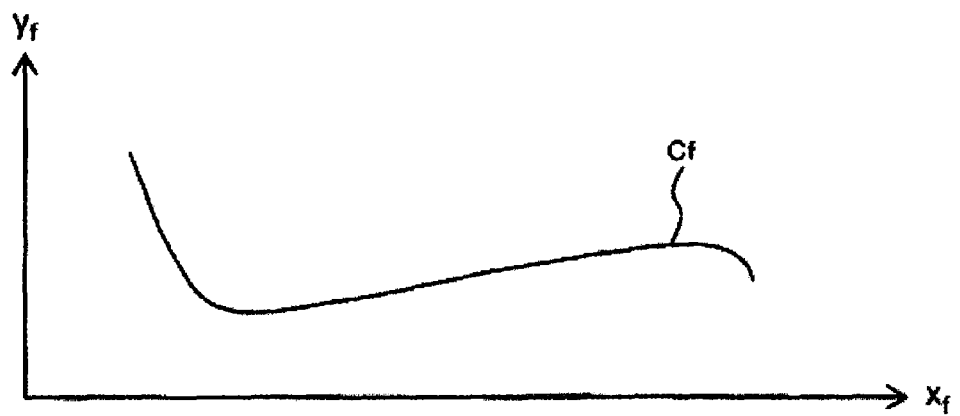
FIG. 9A is a drawing showing a two-dimensional curve based on the wire image in one of the two adjacent frames shown in FIG. 7.
Figure 9B:
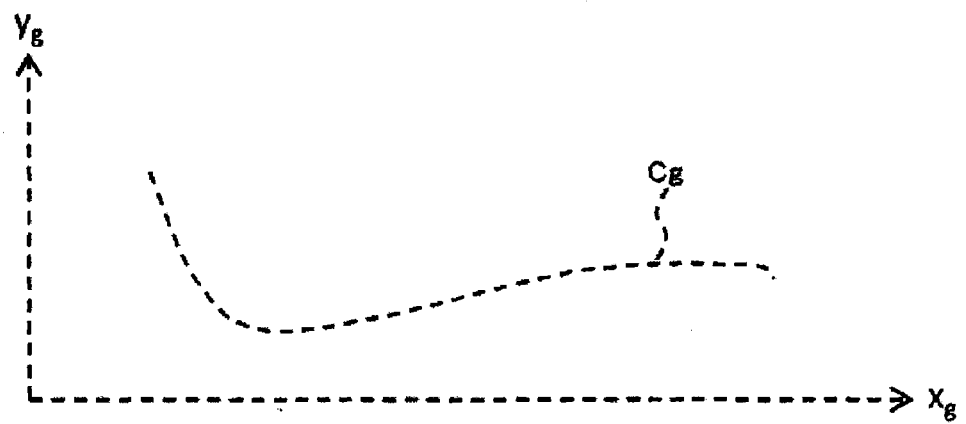
FIG. 9B is a drawing showing a two-dimensional curve based on the wire image in the other of the two adjacent frames shown in FIG. 7.

First, an overview of the process of aligning two adjacent frames is described. The two-dimensional curves based on the wire images C in the adjacent frames f, g shown in FIG. 7 are shown in FIG. 9A and FIG. 9B, respectively. FIG. 9A shows a two-dimensional curve Cf corresponding to the frame f, and FIG. 9B shows a two-dimensional curve Cg corresponding to the frame g. With consideration of the overlapping described below, the two-dimensional curve Cf is represented as a solid line, and the two-dimensional curve Cg is represented as a dotted line. The same applies for the coordinate axes of each diagram.

Next, the alignment processor 43 obtains a coordinate transformation that results in the best match between the two two-dimensional curves Cf, Cg. This coordinate transformation includes parallel displacement and rotational transfer. This type of coordinate transformation may be expressed as an affine transformation. However, the affine transformation used here does not include enlargement/reduction and mirroring.

The obtained affine transformation causes the wire image C of the frame g to undergo relative parallel displacement and/or rotational transfer in accordance with the wire image C of the frame f. This affine transformation is represented by T (g, f).

Figure 10:
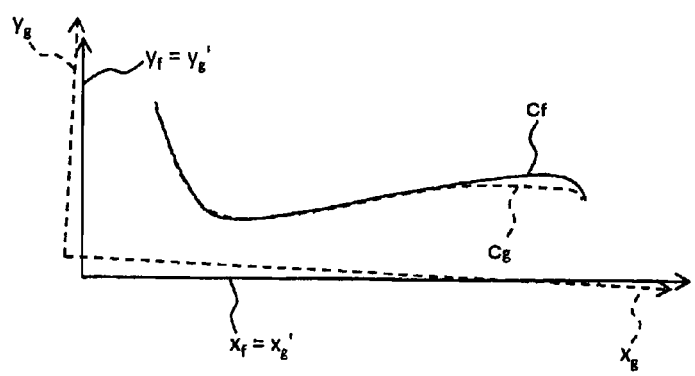
FIG. 10 is a diagram showing the two-dimensional curve shown in FIG. 9A and FIG. 9B in a superimposed state.

When determining the affine transformation T (g, f), it is necessary to consider the effect of changes in shape caused by the movement of the wire inside the body. Therefore, instead of matching the two-dimensional curves Cf, Cg in their entirety, misalignments generated in both end portions are allowed. In particular, for the apical portion, because drastic changes in shape may occur as described above, comparatively large misalignments are allowed. For example, as shown in FIG. 10, for the apical portions of the two-dimensional curves Cf, Cg, it is not necessary to superimpose them as accurately as for other portions.

The alignment processor 43 generates weighting functions $W_f$, $W_g$ corresponding to the respective positions of the two-dimensional curves Cf, Cg.

Generally, the weight is set high for parts that are to undergo precise superimposition, and the weight is set low for parts where misalignments are allowed. For the proximity of the apical portion of the wire, because changes in shape occur easily as described above, the weight is set low. Moreover, it is possible to assign weights according to the degree of curvature at each point in the wire. For example, it is desirable to set the weight high for positions where the curvature of the wire is high. The weighting functions $W_f$, $W_g$ are generated by appropriately setting the weight for each position with consideration of these matters.

For the frame g, because superimposition is performed by applying the affine transformation T (g, f) shown in Formula (1), it is necessary to appropriately determine the parameters θ, u, v. Here, the parameter θ represents the amount of rotational transfer, and the parameters u, v represent the amount of parallel displacement.

[Formula 1]

$$T(g,f) = \begin{pmatrix} \cos\theta & -\sin\theta & u \\ \sin\theta & \cos\theta & v \\ 0 & 0 & 1 \end{pmatrix} \quad (1)$$

The two-dimensional curve obtained by applying the affine transformation T (g, f) to the two-dimensional curve $(x_g, y_g)$ of the frame g is represented as $(x_g', y_g')$. By defining an evaluation of the degree of mismatch between the two-dimensional curve $(x_f, y_f)$ of the frame f and the two-dimensional curve $(x_g', y_g')$ based on an appropriate criterion as E, the parameters θ, u, v are generally calculated so that the value of E becomes almost minimal.

As a more specific configuration, the following example may be used. When the distance between a point p on the two-dimensional curve $(x_f, y_f)$ and a point q that is on the two-dimensional curve $(x_g', y_g')$ and is closest to the point p is defined as D, the following formula is taken into consideration as the evaluation criterion E of the degree of mismatch.

[Formula 2]

$$E = \sum_C DW_f W_g \qquad (2)$$

The sum shown in Formula (2) is obtained for all points on the two-dimensional curve $(x_f, y_f)$. Because the value of E changes when the values of θ, u, and v are changed, values that keep the value of E as low as possible are searched for θ, u, and v. This search is executed using a known technique, such as the nonlinear least-squares method.

An appropriate affine transformation T (g, f) is determined as described above. When this is applied to the frame g, the respective wire images C of the frame f and the frame g are almost completely superimposed, and consequently, these frames f, g are aligned. Furthermore, in the above example, the parameters of the affine transformation are calculated to keep the degree of mismatch as low as possible, but needless to say, a configuration may be used in which, conversely, the degree of matching is evaluated with an appropriate criterion and the parameters of the affine transformation are obtained so that the degree of matching is as high as possible.

In the above calculations, alignment of two adjacent frames is executed. In the present embodiment, because frames are formed sequentially in chronological order, in order to suppress motion of the wire image C in the moving images, it is necessary to sequentially accumulate the affine transformation described above. For this purpose, the alignment processor 43 executes a process such as the following.

The frame immediately before the first frame for which a process for suppressing motion is performed is defined as frame F0, and subsequent frames are sequentially defined as frame F1, F2, F3, etc. (not shown). Here, when the affine transformation applied to the frame Fn (n=1, 2, 3, etc.) is defined as $T_n$, the alignment processor 43 obtains each affine transformation $T_n$ using the following formula.

[Formula 3]

$$T_1 = T(1,0)$$

$$T_n = T(n, n-1) T_{n-1} \qquad (3)$$

By sequentially applying the affine transformation $T_n$ that is sequentially obtained in this way to the corresponding frame Fn, the alignment processor 43 executes alignment of multiple sequentially obtained frames in real time.

In this way, after the following frame g is aligned to the first frame f, the frame h following the frame g is aligned to "the frame g which has been aligned to the first frame f". Consequently, the frame h is almost correctly aligned to the frame f. The same applies subsequently. In this way, it is possible to generate moving images in which the wire image C is almost still. As a result, in X-ray fluoroscopy images observed in real time during catheterization under X-ray fluoroscopy, it becomes possible to suppress movement of the wire image caused by motion of the subject.

In the alignment process described above, when the respective wire images C of the frame f and the frame g are almost completely superimposed, values that kept the evaluation criterion E for the degree of mismatch as low as possible are retrieved for the parameters θ, u, v. These parameters θ, u, v correspond to the amount of change in the shape of the wire when the operator manipulates (axially rotated, advanced, or retracted) the wire. Consequently, based on the parameters θ, u, v, it is possible to detect the amount of change in the shape of the wire.

Next, an example of operations by which the detector 33 detects the amount of change in the shape of the wire based on the parameters θ, u, v is shown.

Here, in moving images obtained at a prescribed frame rate, the parameters θ, u, v retrieved when superimposing the respective wire images of the most recently obtained frame and the frame obtained immediately before are used, as are parameters θ', u', v' retrieved when superimposing the respective wire images of the frame obtained immediately before and the frame retrieved immediately before that one. Based on these parameters θ, u, v and θ', u', v', the detector 33 obtains the residual error of the mean square as shown below.

First, the detector 33 obtains the mean parameter values $θ_a$, $u_a$, $v_a$ through the following calculation.

[Formula 4]

$$θ_a = (θ + θ')/2$$

$$u_a = (u + u')/2$$

$$v_a = (v + v')/2 \qquad (4)$$

Next, through the following calculation, the sum of squares S of the parameters θ, u, v and θ', u', v' for the mean values $θ_a$, $u_a$, $v_a$ is obtained.

[Formula 5]

$$S = (θ-θ_a)^2 + (u-u_a)^2 + (v-v_a)^2 + (θ'-θ_a)^2 + (u'-u_a)^2 + (v'-v_a)^2 \qquad (5)$$

Next, the detector 33 obtains the residual error R of the mean square through the following calculation.

[Formula 6]

$$R = S/D$$

$$D = N*(n-1) \qquad (6)$$

It should be noted that D represents the degree of freedom, which is the number of independently selectable variables, N represents the number of groups, which is the number of sets when observational data are coupled through one calculation, and n represents the observed value, which is the number of observational data included in a single group. Here, N=3 and n=2.

Based on calculations using the Formulae (4) through (6) described above, the detector 33 obtains the residual error R.

(Information for Determining Importance Levels)

The residual error R obtained in this manner acts as information for determining whether or not to increase or decrease the current X-ray dosage.

The X-ray dosage determining part 25 uses a predefined threshold value as a judgment standard and determines whether the residual error R exceeds the threshold value, and when a determination result that the residual error R does not exceed the threshold value is obtained, it determines whether there is scope to reduce the current X-ray dosage. Furthermore, when the X-ray dosage determining part 25 determines whether or not there is scope to reduce the current X-ray dosage, the tube current and the frame rate are used as information for making the determination. If the X-ray dosage determination part 25 determines that the tube current and the frame rate are at the minimum values, the system controller 21 maintains the current X-ray dosage without outputting a control signal for reducing the tube current and a control signal for lowering the frame rate to the high-voltage generator 9. By not reducing the tube current, decreases in the image quality of the X-ray fluoroscopy images are prevented, and by not lowering the frame rate, the moving images are prevented from not operating smoothly. On the other hand, if the X-ray dosage determination part 25 determines that at least one of either the tube current or the frame rate is not the minimum value, the system controller 21 outputs a control signal for reducing the tube current to the high-voltage generator 9 and reduces the tube current.

On the other hand, upon receiving a determination result from the X-ray dosage determination part 25 that the residual error R exceeds the threshold value, if the current tube current and frame rate are both at the maximum levels (set value), the system controller 21 maintains the current X-ray dosage without outputting a control signal for increasing the tube current and a control signal for raising the frame rate to the high-voltage generator 9. If at least one of either the tube current or the frame rate is not the maximum value, the system controller 21 outputs a control signal for increasing the tube current or a control signal for raising the frame rate to the high-voltage generator 9 and increases the X-ray dosage.

The X-ray dosage size that is thus increased or decreased or maintained acts as one item of information for deducing what the staff, including the operator, were doing at the time of the X-ray dosage during catheterization under X-ray fluoroscopy. For the X-ray dosage size, an X-ray dosage size obtained based on the tube current and tube voltage may be used, or control signals that control the high-voltage generator 9 and corresponds to the X-ray dosage size may be used. Subsequent references to "X-ray dosage size" may include these control signals.

Because increases and decreases in X-ray dosage appear as the amount of change in the pixel values of the X-ray images, the amount of change in the pixel values of the X-ray images at the time of acquisition acts as information for deducing the working state at the time of the staff, including the operator. Moreover, for example, based on the fact that the pixel values of X-ray images change due to the administration of a contrast agent, by using the amount of change in the pixel values of the X-ray images at the time of administration of the contrast agent, it becomes possible to deduce whether the staff have administered the contrast agent during catheterization under X-ray fluoroscopy.

Furthermore, the amount of change in the shape of the wire acts as information for deducing wire manipulations by the operator. Although it is also possible to use the X-ray dosage size or the amount of change in the pixel values of the X-ray images as information for deducing whether or not the operator has manipulated the wire, an increase in X-ray dosage does not necessarily mean a wire manipulation, and a great amount of change in the pixel values of the X-ray images does not necessarily indicate wire manipulation, and wire manipulations by the operator do not necessarily correspond to the X-ray dosage size or the amount of change in the pixel values of the X-ray images. In this regard, because the amount of change in the shape of the wire directly represents wire manipulations by the operator, it corresponds to wire manipulations by the operator.

The X-ray dosage size, the amount of change in the pixel values of the X-ray images (administration of contrast agent), and the amount of change in the shape of the wire described above act as information for deducing important scenes or shots representing turning points during catheterization under X-ray fluoroscopy.

(Functions for Deducing Importance Levels and Determining Comprehensive Importance Levels)

In the present embodiment, the importance-level determination part 27 deduces importance levels based on multiple items of information for making a determination, and by synthesizing the deduced importance levels, determines the comprehensive importance level of the X-ray images.

Figure 11:
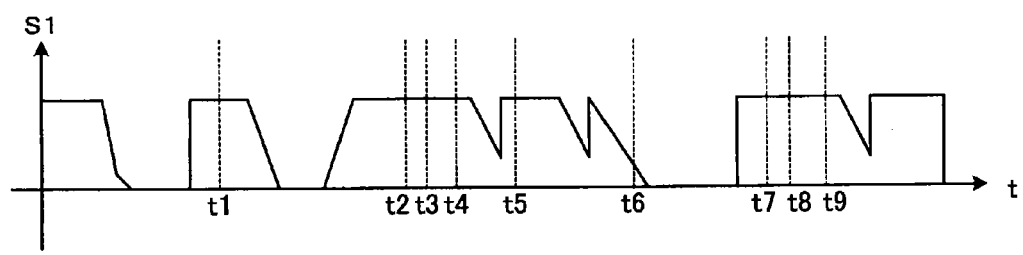
FIG. 11 is a diagram showing importance levels deduced based on the X-ray dosage size.

An example will now be described in which the X-ray dosage size is used as information for deducing importance levels. The system controller 21 associates the X-ray dosage size at the time of acquiring the X-ray images with the acquired X-ray images, and stores them in the memory 22. FIG. 11 shows importance levels deduced by the importance-level determination part 27 based on the X-ray dosage size. FIG. 11 is a diagram in which the horizontal axis is the time axis and the vertical axis indicates importance level, and shows, in correspondence with when the X-rays were irradiated, the importance levels deduced based on the X-ray dosage at the time. As can be seen in FIG. 11, when the X-ray dosage is at the maximum value, the importance level is at the highest, and when X-rays are not irradiated, the importance level is at the lowest.

Next, an example is described in which the acquisition period of X-ray image during catheterization under X-ray fluoroscopy is used as information for deducing importance levels. For the detector 33 that detects the acquisition period of X-ray images, the technology described in, for example, Japanese published unexamined application 2008-301984 is used. In other words, the detector 33 includes a means of keeping the current time, and assigns an acquisition time to each X-ray image included in a group of X-ray images acquired chronologically. The detector 33 may be configured to assign a single acquisition time of an X-ray image as well as a frame rate.

The importance-level determination part 27 deduces the importance level based on a time (hereinafter referred to as "elapsed time") indicating where the acquisition time of the X-ray image is positioned within all periods from the start of acquisition to the end. The importance-level determination part 27 obtains all of the periods based on data at the time of acquisition initiation and data at the time of acquisition completion (both of which are associated with the X-ray images and stored in the memory 22). The importance-level determination part 27 deduces the importance level of the X-ray image in accordance with the elapsed time at which the X-ray image was acquired.

Figure 12:
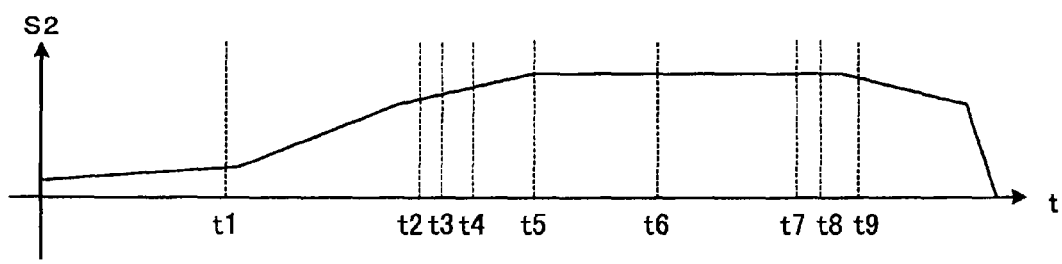
FIG. 12 is a diagram showing importance levels deduced based on the elapsed time in catheterization under X-ray fluoroscopy.

FIG. 12 shows importance levels deduced based on the elapsed time. FIG. 12 is a diagram in which the vertical axis indicates the importance level and the horizontal axis is the time axis, and shows the importance levels deduced by the importance-level determination part 27 based on the acquisition times of the X-ray images during surgery. As can be seen in FIG. 12, the importance-level determination part 27 deduces the importance level of the X-ray image as low in the opening of elapsed time, deduces that the importance level of the X-ray images gradually increases from the opening to the middle, and deduces that the importance level of the X-ray images is maintained at a high level from the middle to the end. This deduction of the importance levels by the importance-level determination part 27 is based on the empirical finding that important scenes and shots representing turning points occur more often between the middle and the end compared to the opening.

Next, an example is described in which the amount of change in the pixel values of X-ray images acquired chronologically is used as information for deducing importance levels. Examples of the detector 33 that detects the amount of change in pixel values include the technology described in Japanese published unexamined application 2009-240559. In other words, it focuses on a target portion within the X-ray images, calculates and compares the pixel values of the target portion in each of multiple temporally continuous X-ray images, and calculates the amount of change over time in the pixel values at the target portion. It should be noted that the amount of change may be calculated based not on a target portion but on aggregate or average values of the pixel values of entire X-ray images. The system controller 21 stores the amount of change in the pixel values of the X-ray images (or the target portion) that has been calculated in this manner in the memory 22, and the importance-level determination part 27 deduces the importance levels based on the amount of change in these pixel values.

Figure 13:
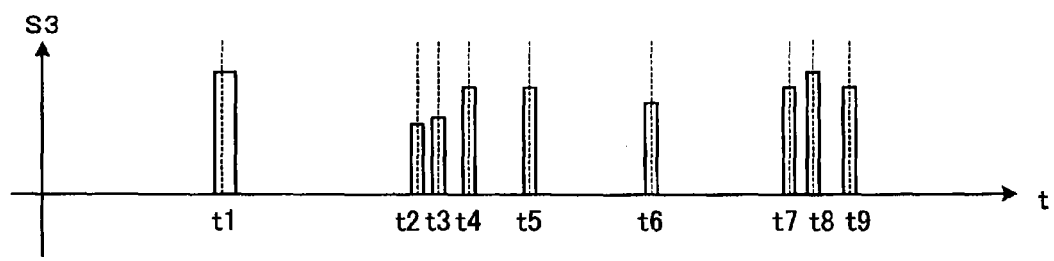
FIG. 13 is a diagram showing importance levels deduced based on the amount of change in the pixel values of an X-ray image.

FIG. 13 shows importance values deduced based on the amount of change in the pixel values of the X-ray images. FIG. 13 is a diagram in which the horizontal axis is a time axis and the vertical axis shows the importance level, and shows the importance levels deduced by the importance-level determination part 27 based on the amount of change in the pixel values of the X-ray images at the positions of the acquisition times of each X-ray image. For ease of explanation, in FIG. 13, the importance levels deduced based on the amount of change in the pixel values of the X-ray images are represented by the length of the bar lines.

Next, an example is described in which, as described above, the amount of change in the shape of the wire is used as information for deducing importance levels. In other words, the system controller 21 stores the residual error R obtained through calculations using the Formulae (4) through (6) described above in the memory 22. The residual error R is associated with the newest of the three frames used to obtain the residual error R, and they are stored in the memory 22. The importance-level determination part 27 deduces the importance levels based on the residual error R. The importance-level determination part 27 deduces that the importance level is high when the residual error R is great. Moreover, the importance-level determination part 27 deduces that the importance level is at a fixed maximum value when the size of the residual error R exceeds a prescribed upper limit.

A diagram showing importance levels deduced based on the amount of change in the shape of the wire (i.e., the size of the residual error R) is, for example, a diagram in which the vertical axis shows the importance level and the horizontal axis is a time axis, showing the importance levels deduced based on the amount of change in the shape of the wire at the positions of the times on the time axis at which those amounts of change occurred. It should be noted that FIG. 13 may be used as a diagram showing importance levels deduced based on the amount of change in the pixel values of the X-ray images as well as the amount of change in the shape of the wire.

Figure 14:
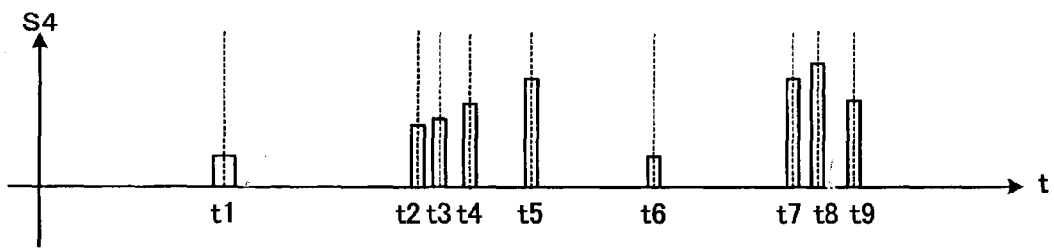
FIG. 14 is a diagram showing comprehensive importance levels determined by synthesizing the deduced importance levels.

Using the above size of the X-ray dosage, the acquisition time of the X-ray images, the amount of change in the pixel values of the X-ray images (administration of a contrast agent), and the amount of change in the shape of the wire as information for making a determination, the importance-level determination part 27 deduces each importance level, and determines a comprehensive importance level based on each importance level. FIG. 14 shows each importance level and the comprehensive importance levels. For ease of explanation, in FIG. 14, the comprehensive importance levels are shown as bar lines. In FIG. 14, from the middle to the end of the acquisition period of the X-ray images, multiple high comprehensive importance levels (long bar lines) are present, and this shows that from the middle to the end, many important scenes and shots deduced to represent turning points were occurred. Consequently, by displaying multiple X-ray images with high comprehensive importance levels as thumbnails in a list, it becomes possible for the operator to recall the important scenes and the shots representing turning points from the thumbnails.

(Function for Selecting Comprehensive Importance Level)

For the operator to recall important scenes, etc. from the thumbnails displayed in a list, it is necessary to select multiple (e.g., 10 or 100) comprehensive importance levels in descending order from among the comprehensive importance levels determined by the importance-level determination part 27, and display the X-ray images of the selected comprehensive importance levels as thumbnails.

Here, after selecting all of the multiple comprehensive importance levels, the X-ray images of the selected comprehensive importance levels may all be displayed as thumbnails, or, after first selecting the highest comprehensive importance level and displaying the X-ray image of the selected highest comprehensive importance level as a thumbnail, the remaining number (e.g., 9 or 99) of comprehensive importance levels may be selected and the X-ray images of the selected remaining number of comprehensive importance levels may all be displayed as thumbnails.

In the present embodiment, after the selection part 26 selects all of the multiple comprehensive importance levels, the display controller 24 displays all of the X-ray images of the selected comprehensive importance levels as thumbnails on the display 31.

Figure 15:
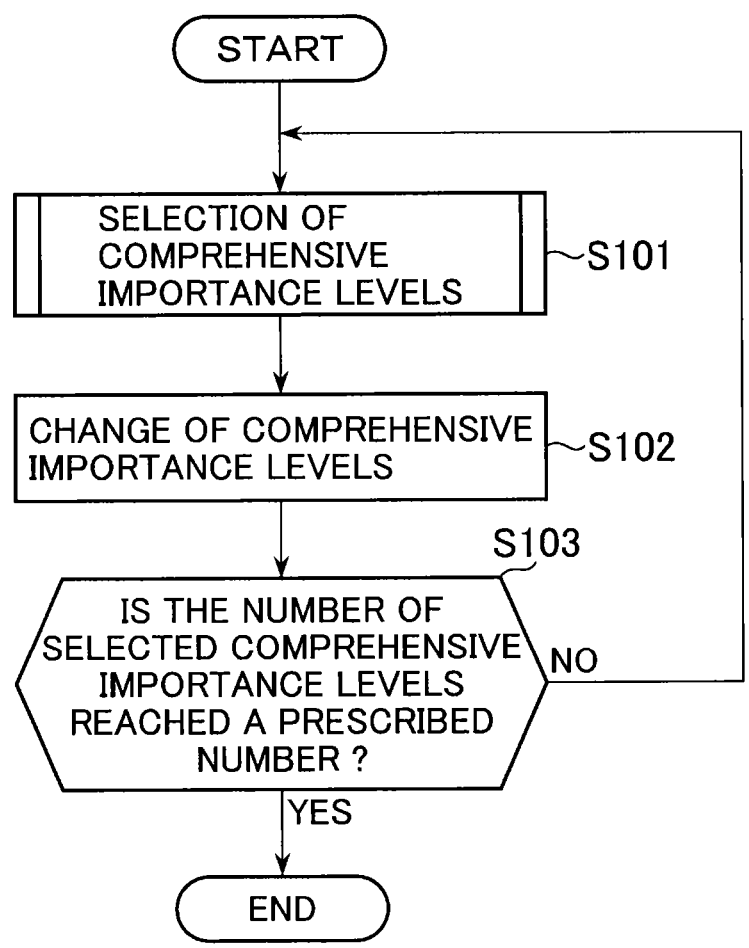
FIG. 15 is a flowchart showing operations performed when selecting multiple importance levels.

Next, operations performed when the selection part 26 selects multiple comprehensive importance levels will be described with reference to FIG. 15 to FIG. 20. FIG. 15 is a flowchart showing all operations performed when selecting multiple X-ray images.

Figure 16:
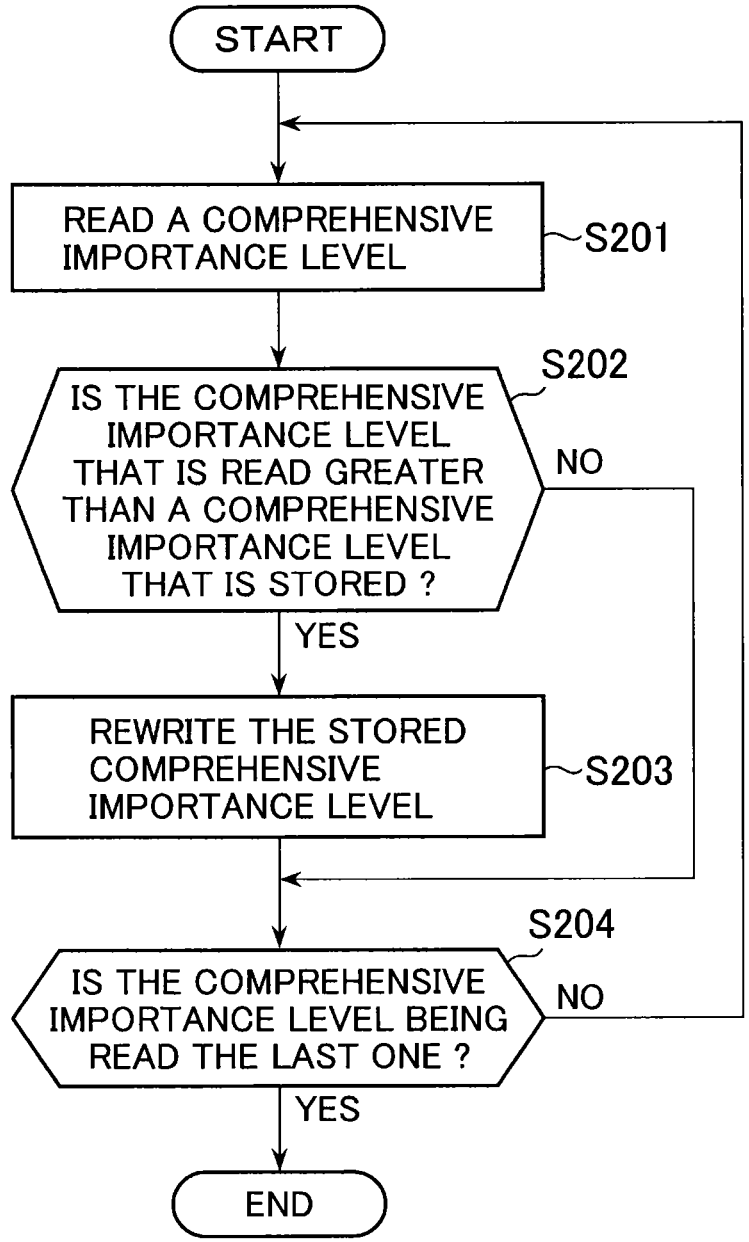
FIG. 16 is a flowchart showing operations performed when selecting individual importance levels.

First, the selection part 26 selects comprehensive importance levels (S101 in FIG. 15). This selection of comprehensive importance levels will be described with reference to FIG. 16. FIG. 16 is a flowchart showing operations performed when selecting a single comprehensive importance level.

The selection part 26 reads a comprehensive importance level stored in the memory 22 in order (i.e., in the order of acquisition) (S201). Next, the selection part 26 determines whether the comprehensive importance level that has been read is greater than a comprehensive importance level stored in a memory (e.g., the internal memory of the arithmetic and control unit 20 or the selection part 26) (S202). If the selection part 26 determines that it is greater (S202: Yes), it rewrites the stored comprehensive importance level (S203). Next, the selection part 26 determines whether the comprehensive importance level of the X-ray image being read is the last one (S204). On the other hand, if the selection part 26 determines that it is the same or lower (S202: No), it proceeds to determine whether the comprehensive importance level being read is the last one (S204).

If the selection part 26 determines that it is not the last one (S204: No), the process returns to reading the comprehensive importance level of the X-ray image (S201). If the selection part 26 determines that it is the last one (S204: Yes), the selection part 26 ends the comprehensive importance level stored in the memory, and ends the selection of the comprehensive importance level. Through the above processes, a single comprehensive importance level is selected.

Figure 18:
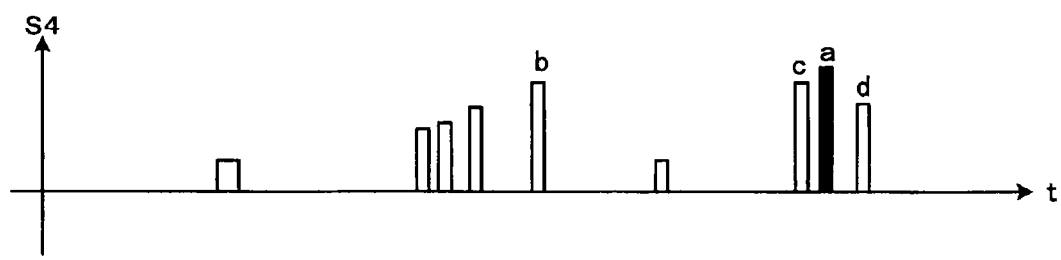
FIG. 18 is a diagram showing a comprehensive importance level that has been determined.
Figure 19:
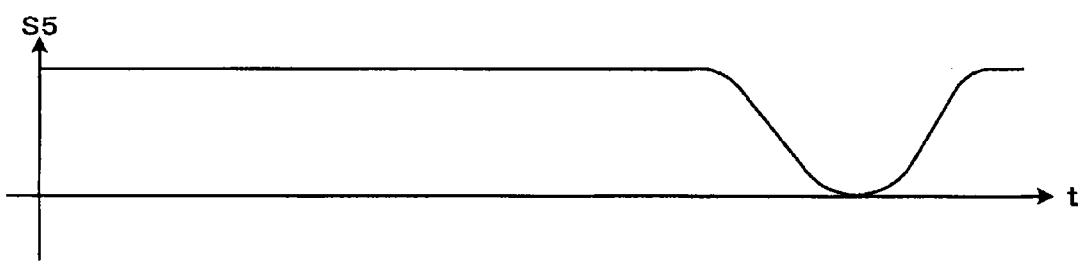
FIG. 19 is a graph representing the mathematical formula used when changing the comprehensive importance level.
Figure 20:
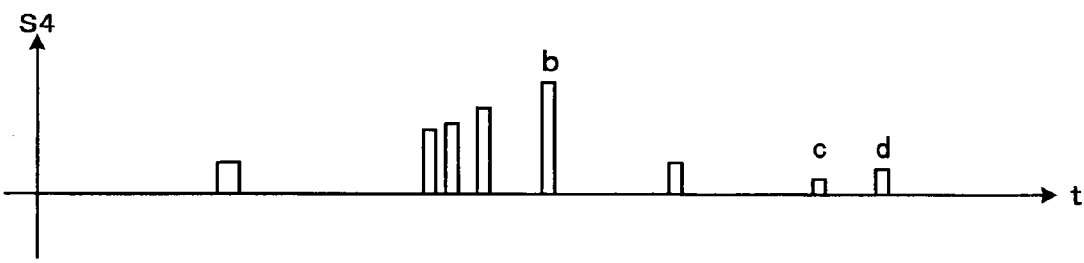
FIG. 20 is a diagram showing a comprehensive importance level that has been changed.

Next, the importance-level determination part 27 changes other comprehensive importance levels based on the selected comprehensive importance level (S102 in FIG. 15). These changes in the comprehensive importance levels are described with reference to FIG. 18 to FIG. 20. FIG. 18 is a diagram showing comprehensive importance levels determined by the importance-level determination part 27, FIG. 19 is a graph representing a mathematical formula used when changing comprehensive importance levels, and FIG. 20 is a diagram showing comprehensive importance levels that have been changed. For ease of explanation, in FIG. 18 and FIG. 20, the comprehensive importance levels are shown as bar lines.

When changing comprehensive importance levels, if, for example, the selection part 26 selects the highest comprehensive importance level (the comprehensive importance level indicated as "a" in FIG. 18), the importance-level determination part 27 uses the prescribed mathematical formula shown in FIG. 19 (shown in FIG. 19) and changes the comprehensive importance levels to lower the comprehensive importance levels of X-ray images acquired near the time at which the selected X-ray image was acquired. As a result, the comprehensive importance levels of "c" and "d", which are near in terms of time, are lowered, and the comprehensive importance level of "b", which is separated from "a" in terms of time, is not changed (shown in FIG. 20). As a result, the comprehensive importance level of "b" becomes relatively higher than the comprehensive importance level of "c", and becomes the next comprehensive importance level to be selected.

After performing the above changes in the comprehensive importance levels (S102), the selection part 26 determines whether the selected comprehensive importance levels have reached a prescribed number (S103). If the selection part 26 determines that the prescribed number has not been reached (S103: No), the selection part 26 returns to selecting a comprehensive importance level (S101), and when the comprehensive importance levels are in the state shown in FIG. 20, for example, the comprehensive importance level of "b" is selected. In this way, the comprehensive importance levels are selected in descending order by the selection part 26. If the selection part 26 determines that the selected comprehensive importance levels have reached the prescribed number (S103: Yes), the selection by the selection part 26 is ended. Based on the above, the prescribed number of comprehensive importance levels is selected.

(Function for List-Displaying X-Ray Images)

Figure 21:
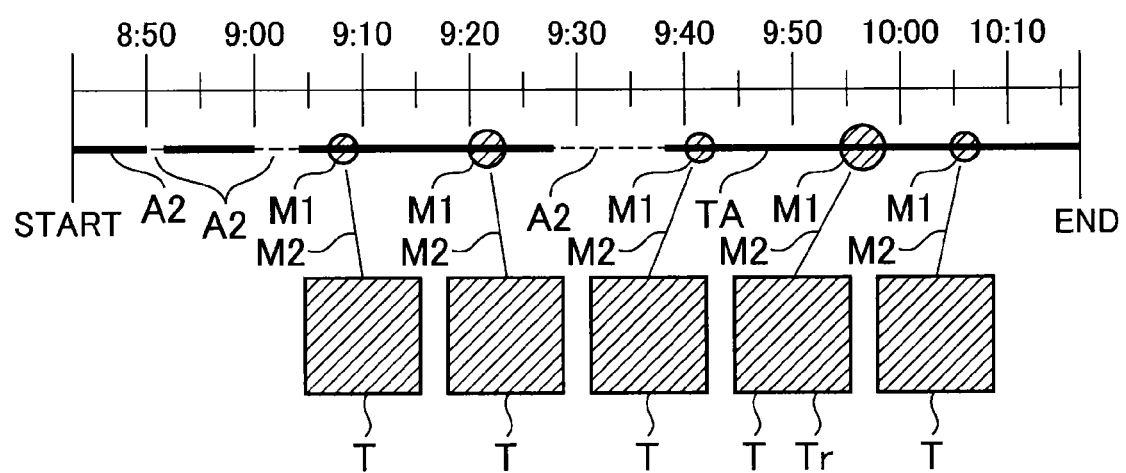
FIG. 21 is a diagram showing X-ray images list-displayed as thumbnails.

Next, after selecting the prescribed number of comprehensive importance levels, the process of displaying the X-ray images of the selected comprehensive importance levels in a list as thumbnails is described with reference to FIG. 21. FIG. 21 is a diagram showing X-ray images displayed in a list as thumbnails. The X-ray images displayed as thumbnails are indicated as "T" in FIG. 21.

After the prescribed number of comprehensive importance levels has been selected by the selection part 26, the display controller 24 reads out the data of the X-ray images corresponding to the selected comprehensive importance levels from the memory 22, and displays those X-ray images in a list as thumbnails on the display 31. The display controller 24 and the display 31 are an example of the "display means" of the present invention.

The display controller 24 associates the multiple X-ray images with a timescale and displays them. As an example of the timescale, a time axis in which a time measure is shown on an axis is used. The display controller 24 displays the time axis, and displays each X-ray image displayed as a thumbnail by associating it with the point on the time axis corresponding to the acquisition time of the X-ray image. As a result, the operator is able to know the relationship between the time represented by the point on the time axis and the X-ray image displayed as a thumbnail that was acquired at that time, and it becomes easy to recall operations performed around the acquisition time of the X-ray image. Here, the process of displaying by associating with the point on the time axis refers to representing the point on the time axis with a mark, or indicating the point with a mark and displaying the X-ray image by associating it with the mark. In the present embodiment, the display controller 24 displays a time axis TA, represents a point on the time axis TA with a mark M1, indicates that point with a mark M2, and associates and displays the circularly shaped mark M1, the mark M2 that is a line connecting that point with the X-ray image, and the X-ray image T that is displayed as a thumbnail. Because the display controller 24 displays the marks M1, M2, it becomes possible to associate the marks M1, M2 with the X-ray image, as well as to associate the marks M1, M2 with the point on the time axis TA, and to associate the point on the time axis TA with the X-ray image via the marks M1, M2.

Furthermore, in catheterization under X-ray fluoroscopy, if X-ray irradiation is stopped during the period between the start and end of the acquisition of X-ray images, a time at which X-ray images are not acquired is included. If the operator is able to visually confirm this time during which X-ray images are not acquired, it becomes possible to recall operations performed around this time, and it becomes possible to easily determine whether desired examination records or desired footage have been recorded.

The display controller 24 displays the parts corresponding to the times during which X-ray images were acquired (indicated by the solid lines A1 in FIG. 21) and the parts corresponding to the times during which they were not acquired (indicated by the dotted lines A1 in FIG. 21) in different modes on the time axis TA or along the time axis TA. Moreover, the display controller 24 associates times with multiple points on the time axis TA and displays times corresponding to each point.

Because the display controller 24 displays the selected multiple X-ray images in a list as thumbnails, it becomes somewhat easier to find desired examination records, etc., but in order to efficiently find desired examination records, etc., rather than browsing the list-displayed X-ray images based on the operator's instinct, it is better to browse based on comprehensive importance levels that are related to the desired examination records, etc. By associating and displaying the X-ray images and their comprehensive importance levels, it becomes possible to browse X-ray images corresponding to the comprehensive importance levels. Because the list-displayed X-ray images are associated with the marks M1, M2, in the present embodiment, the comprehensive importance levels are displayed using the marks M1, M2.

The display controller 24 causes the display 31 to display the marks M1, M2 in a mode corresponding to the height of the comprehensive importance levels. For example, as shown in FIG. 21, the size of the circle of the mark M1 may be made to correspond to the height of the comprehensive importance level. As other modes, the mark M1 may be displayed with different colors (in descending order: red, amber, yellow, green, and blue), or it may be displayed with the different blinking frequencies (making the blinking frequency higher for higher levels).

Furthermore, the comprehensive importance levels may be displayed using the X-ray images. In this case, the display controller 24 causes the display 31 to display the X-ray images in a mode corresponding to the height of the comprehensive importance level. In one example of this display, a mode in which the border thickness of the thumbnails, the color of the borders, and the blinking frequency of the borders are different is used. Moreover, the display controller 24 may display the diagram of FIG. 14 showing the comprehensive importance levels on part or all of the screen of the display 31.

(Other Functions)

In the above, the "functions for deducing importance levels and determining comprehensive importance levels", etc. of the medical imaging apparatus has been described. Next, other functions of the medical imaging apparatus will be described.

When any of the X-ray images displayed in a list as thumbnails is selected by an operating part 32 (e.g., a pointing device), the display controller 24 plays back moving images including the selected X-ray image on the display 31.

Although it is sufficient if the X-ray image is included in any of the moving images that are played back, it is preferable to play back a series of moving images starting from an X-ray image acquired a prescribed time before the acquisition time of the selected X-ray image to an X-ray image acquired a prescribed time after the acquisition time. By looking at the X-ray images acquired around the acquisition time of the selected X-ray image, it becomes possible to recall operations performed around the acquisition time, and it becomes easier to find desired examination records or determine whether desired footage has been recorded. The display controller 24 and the display 31 are an example of the "playback means" of the present invention.

It should be noted that the mode of playback of moving images is not limited to this. For example, after receiving a designation of a point on the time axis TA displayed on the display 31 from the operating part 32, the display controller 24 may cause the display 31 to play back moving images including the X-ray image acquired at the time corresponding to the point on the time axis TA. As a result, it is possible to easily check moving images including X-ray images other than the X-ray images displayed in a list.

Moreover, multiple X-ray images may be selected using the operating part 32. The display controller 24 may automatically splice together moving images including each of these multiple selected X-ray images. Alternatively, the operating part 32 may be used to designate multiple points on the time axis TA, and the display controller 24 may automatically splice together moving images including each of multiple X-ray images corresponding to these multiple points. As a result, it is possible to greatly reduce the time for browsing the moving images.

In the above, functions for deducing importance levels and selecting comprehensive importance levels, the function for displaying X-ray images in a list, and other functions such as the function for playing back moving images have been described. As a result of these functions, it has become possible to automatically select the highest comprehensive importance level, and then automatically select other comprehensive importance levels, display the X-ray images of these selected comprehensive importance levels in a list as thumbnails, and play back moving images from a selected, desired time through easy operations.

At the same time, it is not necessarily the case that the operator will recall important scenes or shots representing turning points based on the X-ray image (indicated as "Tr" in FIG. 21) of the highest comprehensive importance level that has been automatically selected. It may be the case that the operator may better recall important scenes, etc. from other X-ray images.

Therefore, the selection part 26 selects the X-ray image with the highest comprehensive importance level, as a representative thumbnail, from among the multiple X-ray images displayed in a list as thumbnails, and after receiving an instruction from the operating part 32, replaces the representative thumbnail by selecting other X-ray image as a new representative thumbnail. For the other X-ray image, for example, it is sufficient to use an X-ray image (indicated by "T" in FIG. 21) of another comprehensive importance level that is automatically selected after the selection of the highest comprehensive importance level and is displayed in the list together with the X-ray image (indicated by "Tr" in FIG. 21) of the highest comprehensive importance level. In this way, by replacing the representative thumbnail, the other comprehensive importance levels that are subsequently selected are also changed.

Figure 17:
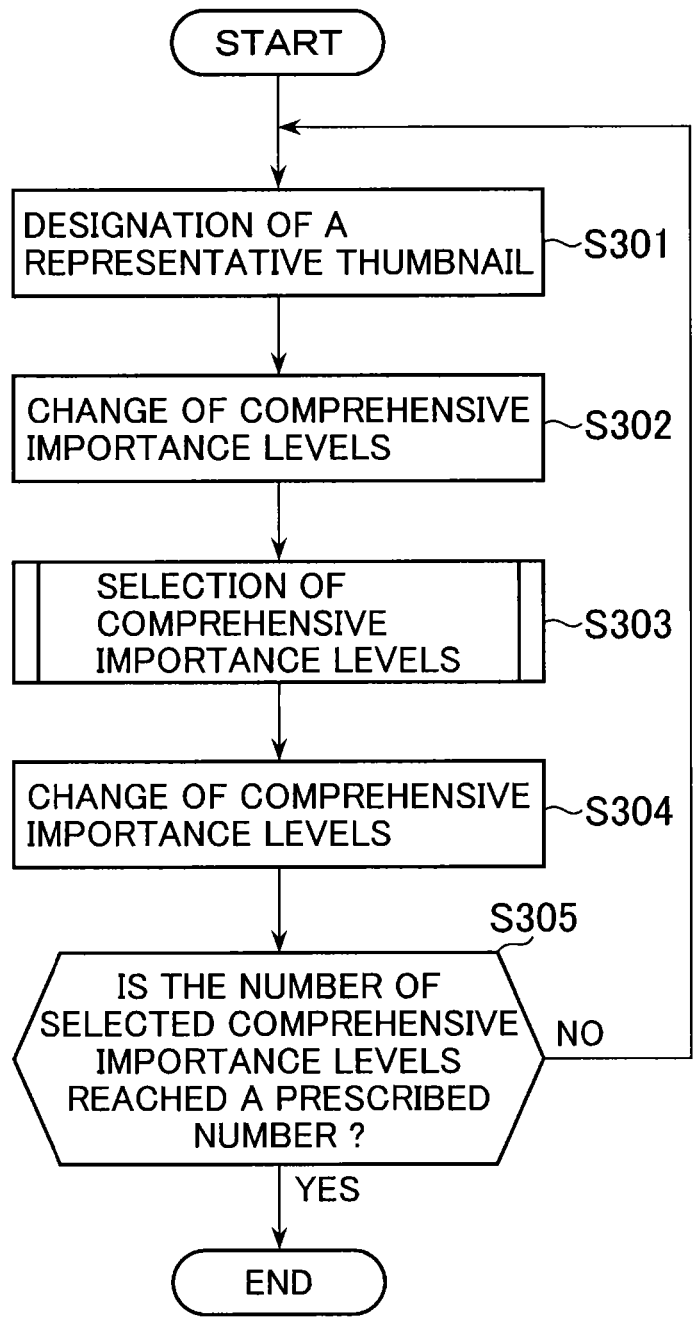
FIG. 17 is a flowchart showing operations performed when designating an X-ray image to be displayed as a representative thumbnail.

Details of the selection of the X-ray image acting as the representative thumbnail, as well as of changes in the other comprehensive importance levels will now be described with reference to FIG. 17. FIG. 17 is a flowchart showing operations performed when designating an X-ray image to be displayed as the representative thumbnail.

When the number of selected comprehensive importance levels reaches a prescribed number (S103: Yes in FIG. 15), the display controller 24 causes the display 31 to display the X-ray images of the selected comprehensive importance levels in a list as thumbnails. Here, the X-ray image of the highest comprehensive importance level is displayed as the representative thumbnail.

To replace the X-ray image displayed as the representative thumbnail with another X-ray image, an X-ray image (indicated by "T" in FIG. 21) that is displayed in the list together with the X-ray image (indicated by "Tr" in FIG. 21) acting as the representative thumbnail is designated using the operating part 32 (S301). Upon receiving the designation from the operating part 32, the selection part 26 changes the comprehensive importance levels (S302). As with S102 (changes in other comprehensive importance levels based on a selected comprehensive importance level) shown in FIG. 15, this change in comprehensive importance levels involves changes in other comprehensive importance levels based on the comprehensive importance level of the designated X-ray image.

Second Embodiment

In the first embodiment, the importance-level determination part 27 deduced each importance level using the size of the X-ray dosage, the acquisition period of the X-ray images, the amount of change in the pixel values of the X-ray images (administration of a contrast agent), and the amount of change in the shape of the wire as information for making a determination, but it is sufficient to use at least one of the manipulated state of an instrument (wire) handled by the operator, biological information of the operator, or the behavior of the operator as information for deducing importance levels. Next, other examples used as information for deducing importance levels will be described.

In the first embodiment, an example was described in which the results of detecting changes in the shape of the wire were used as information for determining whether or not the operator was manipulating the wire, but the results of detecting sounds or vibrations generated when the wire is manipulated may be used as information for determining the manipulated state of the wire, or the results of detecting motion of the hand of the operator manipulating the wire may be used.

Here, an example is described in which the results of detecting sounds and vibrations generated when the wire is manipulated are used as information for making a determination on the manipulated state of the wire. When the wire is manipulated, a valve (not shown) provided inside the adaptor is rubbed with the wire, and sounds and vibrations in a specific frequency band are generated. If the generation of the sounds and vibrations is frequent, it is possible to presume that the operator is manipulating the wire.

Figure 22:
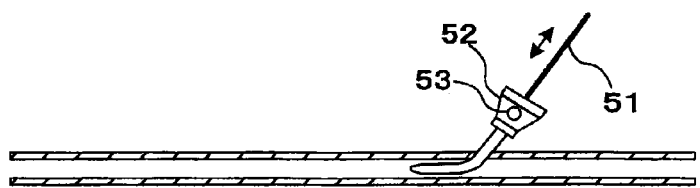
FIG. 22 is a drawing showing an example in which a solid microphone attached to an adaptor is used as an operator sensor according to a second embodiment.
Figure 23:
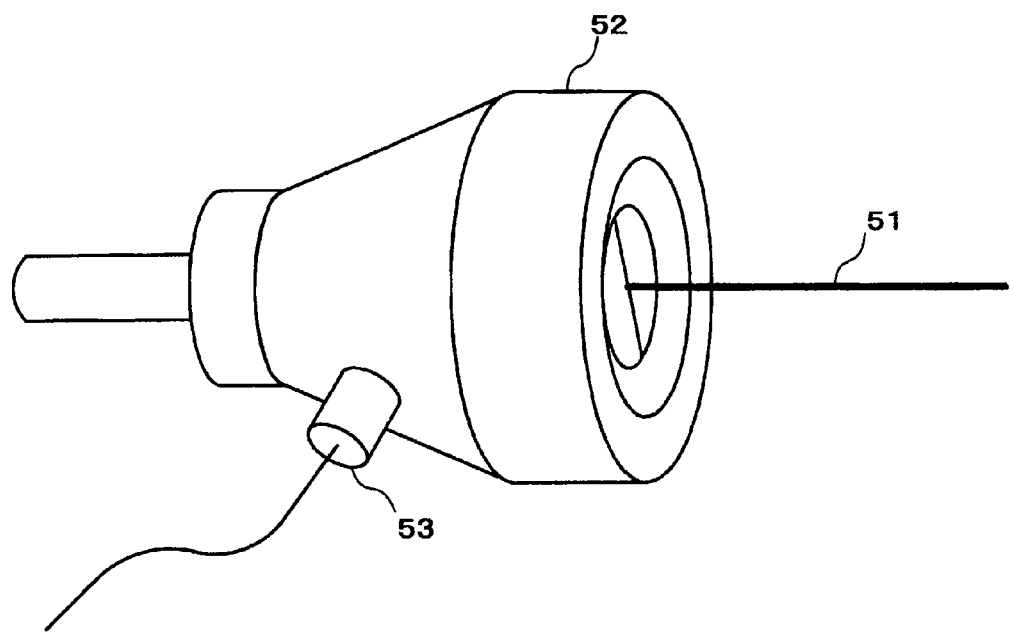
FIG. 23 is a drawing showing an enlargement of the adaptor part shown in FIG. 22.

The details of the present embodiment will now be described with reference to FIG. 22 and FIG. 23. FIG. 22 is a diagram showing an example using a solid microphone attached to the adaptor, and the direction of manipulation of the wire is indicated by the arrow. FIG. 23 is a diagram showing an enlargement of the adaptor part. Sounds and vibrations from the wire 51 grazing the valve are detected by the solid microphone 53 attached to the adaptor 52, and the frequency of wire manipulation is detected. The importance-level determination part 27 determines whether or not this frequency exceeds a predefined threshold value (e.g., N times in 10 seconds), counts the number of times exceeding the threshold value (0, 1, 2 . . . m), and deduces the importance levels of the X-ray images in response to the length of time during which the threshold value is continuously exceeded (e.g., number of times exceeding the threshold value*10 seconds). This length of time during which the threshold value is continuously exceeded is an example of the "length of time of continuous motion of the insert instrument" of the present invention.

Next, an example is described in which the results of detecting motion of the hand of the operator manipulating the wire are used as information for determining the manipulated state of the wire. Using, for example, an infrared-reflection motion sensor attached to the adaptor, motion of the hand of the operator is detected near the adaptor, the mean amount of motion of the hand of the operator is obtained every second, and the number of times that the mean value meets or exceeds a specific amount is detected. Using a predefined threshold value (e.g., N times per 10 seconds) as a judgment standard, the importance-level determination part 27 determines whether or not the detected number of times exceeds the threshold value, and may count the length of time during which the threshold value is continuously exceeded (e.g., number of times exceeding the threshold value*10 seconds). The importance-level determination part 27 deduces the importance levels of the X-ray images in response to the length of time during which the threshold value is continuously exceeded. This length of time during which the threshold value is continuously exceeded is another example of the "length of time of continuous motion of the insert instrument" of the present invention. Here, examples of an infrared-reflection motion sensor include those in which multiple pyroelectric elements are arranged within a detection range set at the focal length of an infrared condenser lens, and motion of the detection subject (i.e., the hand of the operator) is detected as changes in electric quantity with the pyroelectric elements.

It should be noted that, for the detector 33 that detects motion of the hand of the operator manipulating the wire, instead of an infrared-reflection motion sensor, an acceleration sensor may be attached to the hand of the operator. In this case, the acceleration sensor detects the number of times that the acceleration meets or exceeds a specific amount, and the importance-level determination part 27 deduces the importance levels of the X-ray images in response to that number. A predefined threshold value (e.g., N times per 10 seconds) is used as a judgment standard. Here, examples of an acceleration sensor include those that detect positional changes caused by acceleration as changes in diaphragm position by using piezoresistant elements.

Third Embodiment

The medical imaging apparatus according to the second embodiment detects the manipulated state of an instrument (wire) handled by the operator, and using the detection results as information for making a determination, the importance-level determination part 27 deduces the importance levels of the X-ray images. In comparison, as other information for making a determination, the results of detecting the posture of the operator may be used. Furthermore, the importance-level determination part 27 may be configured to deduce the importance levels of the X-ray images using a synthesis of the detection results of the manipulated state of the instrument and the detection results of the posture of the operator as information for making a determination. Furthermore, the comprehensive importance levels may be determined by combining these deduced importance levels with other deduced importance levels. In this way, by combining greater numbers of deduced importance levels, the correspondence between the comprehensive importance levels and the working state of the operator is strengthened. As a result, based on the X-ray images selected by the selection part 26 based on the comprehensive importance levels, it becomes easy to recall the operations performed by the operator at the time of acquisition of those X-ray images. It is possible to easily find a desired examination, and it is easy to determine the location within the examination records where desired footage has been recorded.

As an example of detection results of the posture of the operator, the results of detecting whether or not the operator is viewing a display (the display 31) for displaying X-ray fluoroscopy images may be used. Generally, when the operator approaches the display displaying X-ray fluoroscopy images, or when the operator faces the direction of the display displaying X-ray fluoroscopy images, it may be deduced that the operator is looking carefully at the X-ray fluoroscopy images and that the working state of the operator is nearing an important scene. As an example of information used for determining whether or not the operator has approached the display displaying X-ray fluoroscopy images, measurements may be taken using a sensor, such as a camera, attached to the display. There are the detection results of the position of the operator from the perspective of the display. Moreover, as an example of information for determining whether or not the operator is facing the direction of the display displaying X-ray fluoroscopy images, there are the detection results of the area of the face of the operator facing the display, and the detection results of the orientation of the face of the operator relative to the display. Furthermore, a determination as to whether the operator is viewing the display for displaying X-ray fluoroscopy images may be made by combining any two or more of these detection results as information for making a determination.

Here, an example is described in which the detection results of the position of the operator relative to the display are used as information for determining whether or not the operator has approached the display displaying X-ray fluoroscopy images. The position of the operator relative to the display is detected using an ultrasonic sensor attached to the display. As long as the distance between the display and the operator can be detected, the location for attaching the ultrasonic sensor is not limited to the display, and any location where the relative positions of the display and the operator can be grasped may be used. Furthermore, examples of ultrasonic sensors include those that transmit ultrasound waves from the sensor head, receive ultrasound waves reflected from the subject (i.e., the face of the operator) through the sensor head, and measure the time between the transmission and reflection of the ultrasound waves to detect the position of the subject.

Moreover, the device that detects the position of the operator relative to the display is not limited to an ultrasonic sensor, and may be, for example, a camera with a facial recognition function, for example. The direction from this camera with a facial recognition function to the face of the operator is detected, and based on the detection results, the distance from the screen of the display to the position of the face of the operator is calculated. As an image recognition function, the image processing function described in, for example, Japanese published unexamined application Hei 8-275195, in which a face candidate region is detected by detecting a skin-color region that is characteristic of the face using color-difference images. Furthermore, this camera with a facial recognition function may be one that simply identifies the color of the skin of the operator and detects the position of the face of the operator (i.e., the position of the location where the face of the operator is present) in the image.

Generally, when the face of the operator approaches the display, it is deduced that the operator is performing an important operation and that the importance level of the X-ray image is high. Moreover, when the face of the operator becomes distant from the display (becomes distant along a direction perpendicular to the screen of the display, or becomes distant in a direction at an angle relative to the direction perpendicular to the screen of the display), it can be deduced that the importance level of the X-ray image is low. Consequently, the importance-level determination part 27 obtains the distance from the screen of the display to the position of the face of the operator, and deduces the importance levels of the X-ray images in response to the obtained results.

Fourth Embodiment

In the third embodiment, the importance levels of X-ray images are deduced using the position of the operator relative to the display as information for making a determination. However, there are cases in which the operator may simply approach the display without intending to look carefully at the X-ray images. In this case, the importance levels of the X-ray images cannot be considered high. Therefore, the following is a description of an example in which, by using the detection results of whether or not the operator has faced the direction of the display displaying X-ray fluoroscopy images as information for making a determination, a determination is made as to whether the operator is simply approaching the display or intends to look carefully at the X-ray images.

Figure 24:
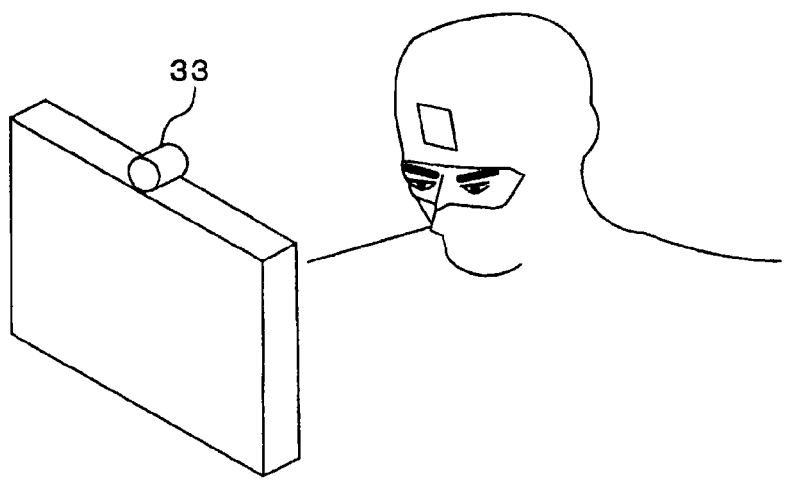
FIG. 24 is a drawing showing an example in which a camera attached to a display is used as an operator sensor according to a fourth embodiment.

Another embodiment of the present invention will now be described. An example will be described in which the orientation of the face of the operator or his/her line of sight is detected as working-state information. An example is described in which detection results of the area of the face of the operator relative to the display are used as detection results for whether or not the operator is facing the direction of the display displaying X-ray fluoroscopy images. The orientation of the face of the operator relative to the display is detected using a camera attached on or near the display. The camera has the image recognition function described earlier. Because the operator is wearing a surgical gown and a mask with a color different from the skin color, the camera identifies the color of the skin of the operator, identifies the position of the color of the skin in the image, and is able to detect the area of the face. If the area of the face is small, it is deduced that the operator is not directly facing the direction of the display. The camera attached to the display and the operator wearing a surgical gown and mask are shown in FIG. 24. Due to the surgical gown and mask, only the areas around the eyes and the nose of the face of the operator are exposed, and the remaining parts are covered. The exposed regions around the eyes and the nose are hereinafter referred to as the "exposed region". The area of the exposed region from the perspective of the camera is detected.

Figure 25:
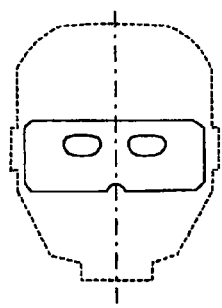
FIG. 25 is a drawing showing the exposed region when the operator faces the display directly.
Figure 26:
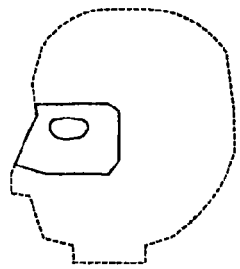
FIG. 26 is a drawing showing the exposed region when the operator does not face the display directly.

The exposed region when viewed from the camera is described with reference to FIG. 25 and FIG. 26. FIG. 25 is a diagram showing the exposed region in a case in which it is deduced that the operator is directly facing the direction of the display, and the contour shape of the exposed region shown enclosed in a solid line is an approximately rectangular shape that is lengthwise in the width direction of the face. FIG. 26 is a diagram showing the exposed region in a case in which it is deduced that the operator is not directly facing the direction of the display, and the contour shape of the exposed region shown enclosed in a solid line is an approximately rectangular shape, but the width direction of the face is shorter compared to the case shown in FIG. 25. The area of the exposed region when viewed from the camera becomes smaller as the operator faces the display more indirectly. Consequently, the importance-level determination part 27 obtains the area of the current exposed region, and deduces the importance level of the X-ray image in response to the ratio of the area of the current exposed region relative to the maximum area of the exposed region (the area of the exposed region when it is deduced that the operator is directly facing the direction of the display). This is because it is deduced that the importance level of the X-ray images increases as the operator faces the direction of the display more directly.

Furthermore, instead of the area of the exposed region, it is possible to detect the exposed region, extract the contour of this exposed region, and use this contour as information for making a determination. With the contour of the exposed region, the image of the exposed region becomes large when the operator approaches the display, and the image of the exposed region becomes small when the operator becomes distant from the display. Therefore, within the contour, using, for example, the length between the lower margin of the cap and the upper margin of the mask (i.e., the vertical length of the approximately rectangular shaped contour) as a standard, the image that is the subject of comparison is enlarged or reduced so that the length thereof becomes equivalent in both images, and the contour after the size adjustment is used as information for making a determination. This image adjustment is also effective when using the area of the exposed region as information for making a determination.

Fifth Embodiment

In the fourth embodiment, an example was described in which the detection results of the area of the face of the operator (the area of the exposed region from the perspective of the camera) relative to the display was used as the detection results of whether or not the operator was facing the direction of the display displaying X-ray fluoroscopy images. However, the area of the exposed region varies for each operator depending on the size and shape of their face, and even for a single operator, variations occur depending on the manner in which the gown and mask are worn. In particular, variations occur when the position of the mask is adjusted during surgery. These variations may interfere with the accurate deduction of the importance levels of the X-ray images. Therefore, in order to accurately deduce the importance levels of the X-ray images, the detection results of the facial orientation of the operator relative to the display are used as information for making a determination.

Figure 27:
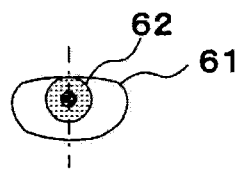
FIG. 27 is a drawing showing an image of an eye when the operator faces the display directly in a fifth embodiment.
Figure 28:
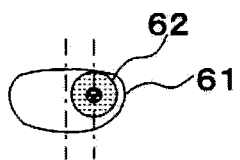
FIG. 28 is a drawing showing an image of an eye when the operator does not face the display directly.

Another embodiment of the present invention will now be described. As another example in which the detection results of whether or not the operator is facing the direction of the display displaying X-ray fluoroscopy images are used as information for making a determination, the detection results of the facial orientation of the operator relative to the display may be used. A camera including a characteristics-detecting mechanism attached to or near the display is used to extract the region of the eyes (iris and sclera) of the operator. For the characteristics-detecting mechanism, the characteristics-detecting mechanism described in Japanese published unexamined application Hei 2004-91917 that extracts the pupil position and the contours of the iris regions from an image is used, for example. For example, the respective regions of the iris (pupil and iris) and the sclera extracted by the characteristics-detecting mechanism are shown in FIG. 27 and FIG. 28. As shown in FIG. 27, in the eye region indicating that the operator is facing the direction of the display, the center of gravity of the iris region 62 is positioned on or near the center line of the width direction (i.e., the direction from the inner corner to the outer corner of the eye) of the sclera region 61. Moreover, as shown in FIG. 28, in the eye region indicating that the operator is not facing the direction of the display, the center of gravity of the iris region 62 is positioned away from the center line of the width direction of the sclera region 61. Consequently, the importance-level determination part 27 deduces the importance levels of the X-ray images in response to the results of detecting the position of the center of gravity of the iris region relative to the center line in the width direction of the sclera region. This is because it is deduced that the importance levels of the X-ray images is higher when the operator is facing the direction of the display more directly.

Sixth Embodiment

In the fifth embodiment, an example was described in which, for the detection results of whether or not the operator was facing the direction of the display displaying X-ray fluoroscopy images, the results of detecting the position of the center of gravity of the iris region relative to the center line in the width direction of the sclera region was used. However, there are individual differences in the size and shape of the eyes (iris region and sclera region) of the operator. Moreover, there are cases in which the conditions for acquiring an image of the eyes of the operator are not good due to such as reflected light from glasses used by the operator. These individual differences between operators and poor conditions during image acquisition cause errors in the detection results to increase, and may reduce accuracy when deducing the importance levels of the X-ray images. To detect with certainty whether or not the operator is facing the direction of the display, a configuration may be used in which a target worn by the operator is detected.

As another example in which detection results of the facial orientation of the operator relative to the display are used as information for making a determination, the detection results of detecting a target worn by the operator are described.

As the target worn by the operator, an example is described in which a reflection marker attached on the median line of the cap or mask, etc. of the operator is used. The reflection marker is, for example, a flexible sheet formed into a rectangular shape, and is a reflective layer composed of metallic thin film of aluminum, etc. formed on the surface of the sheet through, for example, sputtering or an evaporation method, etc. An infrared light source that irradiates infrared light at the reflection marker is mounted on or near the display, and furthermore, a camera that has the frontal region (i.e., a region to which the screen is faced, that is within a specific distance from the screen) of the screen of the display as its imaging field is likewise mounted on or near the display.

Figure 29:
FIG. 29 is a drawing showing a reflection marker worn by the operator in a sixth embodiment.
Figure 30:
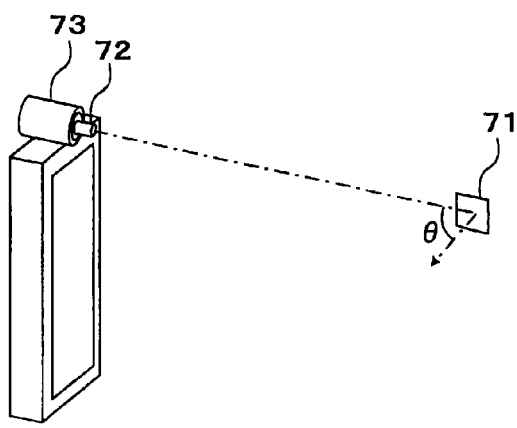
FIG. 30 is a drawing showing an operator sensor and a reflection marker.

For example, as shown in FIG. 29, a reflection marker 71 is mounted on the median line of the cap of the operator. Then, as shown in FIG. 30, the reflection marker 71 mounted on the cap (not shown) of the operator is detected by an infrared light source 72 and a camera 73 mounted on the display. θ is the angle of the reflected infrared light relative to the incident light (i.e., the sum of the incident angle and the reflection angle).

Figure 31:
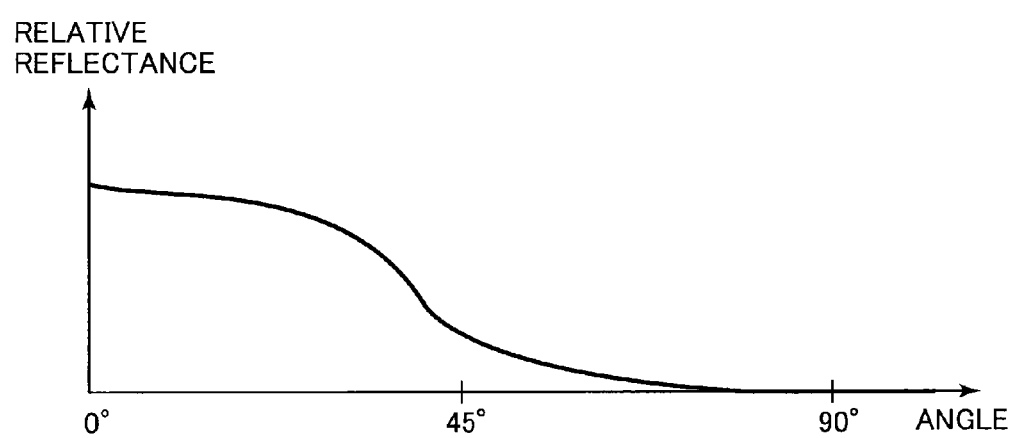
FIG. 31 is a graph depicting the relationship between the angle θ and the relative reflectance with regard to a reflection marker.

Generally, because the reflection marker faces the display more directly when detected amount (by the camera 73) of reflected infrared light from the reflection marker is greater, when the detected amount is greater, it is possible to deduce that the operator is more directly facing the display. Consequently, the importance-level determination part 27 obtains the relative reflectance (i.e., the ratio of the intensity of the current reflected light relative to the intensity of the reflected light when directly faced) from the results of detecting the intensity of the reflected light from the reflection marker, and deduces the importance levels of the X-ray images in response to the relative reflectance. This is because when the relative reflectance is high, it is deduced that the operator is facing the direction of the display and that the importance level of the X-ray image acquired at that time is high. FIG. 31 is a graph depicting the relationship between the angle θ and the relative reflectance. FIG. 31 shows how the relative reflectance is reduced as the angle θ goes from 0° (the angle when the operator is directly facing the display) to 90° (the angle when the operator is facing exactly laterally from the display).

(Variation)

An example using relative reflectance as information for making a determination has been described above, but the present embodiment is not limited to this. When the sum of the luminance of the pixels corresponding to the image of the reflection marker captured by the camera is great, it can be deduced that the operator is directly facing the display. Consequently, the importance-level determination part 27 detects the sum of the luminance of the reflection marker, obtains the ratio of the sum of the luminance (i.e., the ratio of the current sum of the luminance relative to the sum of the luminance when faced directly) from the detection results, and deduces the importance level of the X-ray image in response to the sum of the luminance of those pixels. This is because it is deduced that the importance level of the X-ray image acquired at the time is high when the operator is facing the direction of the display.

Figure 32:
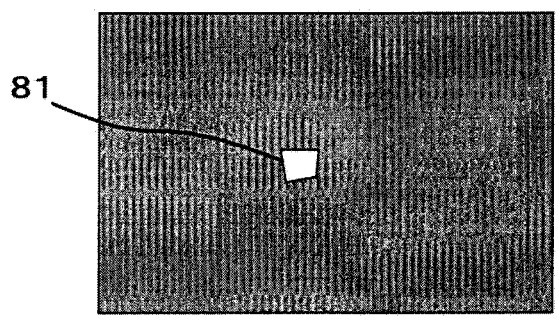
FIG. 32 is a drawing showing an image of a reflection marker when the operator faces the display directly in a variation of the sixth embodiment.
Figure 33:
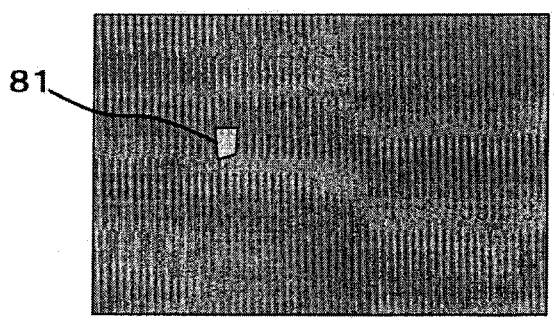
FIG. 33 is a drawing showing an image of a reflection marker when the operator does not directly face a liquid crystal display.

FIG. 32 shows an image of a reflection marker in a case in which it is deduced that the operator is directly facing the display, and the shape of the image 81 of the reflection marker that is shown with highly luminous pixels is almost a copy of the contour shape of the reflection marker. FIG. 33 shows an image of a reflection marker in a case in which it is deduced that the operator is not directly facing the display, and the shape of the image 81 of the reflection marker is narrow in the horizontal direction relative to the contour shape of the reflection marker, and the luminance of the pixels forming the image 81 is lower than the luminance forming the image 81 shown in FIG. 32. Consequently, the image of the reflection marker when it is deduced that the operator is directly facing the display is larger than the image of the reflection marker when it is deduced that the operator is not directly facing the display, and the luminance of the pixels forming the image is also higher.

The detector 33 according to the third through sixth embodiments described above detects whether or not the operator is viewing the display as the posture of the operator. However, the detector 33 that detects the posture of the operator is not limited to this.

Seventh Embodiment

In catheterization under X-ray fluoroscopy, when performing wire manipulations requiring very precise operations, the operator normally does so without making great changes in posture, and the frequency of body motion of the operator is therefore low. Consequently, in catheterization under X-ray fluoroscopy, if body motion of the operator is frequent, they are not performing wire manipulations, and it may therefore be deduced that the importance levels of the X-ray images are low. Focusing on this point, the detector 33 for detecting whether or not body motion of the operator is frequent is provided.

As an example of using the results of detecting whether or not body motion of the operator is frequent as information for making a determination, detection results for detecting the barycenter of the operator by using a pressure sensor mat spread below the feet of the operator are described. Here, "body motion" includes, for example, the operator bending his/her upper body frontward and sideways, as well as the operator changing direction or moving their standing position, and does not include motions typical of wire manipulation, in which mainly only the hands and arms are moved while keeping the upper body still and without changing direction. The pressure sensor mat detects pressure from the feet of the operator as a two-dimensional pressure distribution pattern. The importance-level determination part 27 acquires a two-dimensional pressure distribution pattern in an interval of a fixed time (e.g., 0.1 second), creates pressure distribution pattern images of several (e.g., 30) patterns acquired over a preceding predefined time (e.g., the past 3 seconds), and obtains the barycenter of the operator based on the pressure distribution pattern image. Here, as an example of the pressure sensor mat, the pressure-receiving surfaces of semiconductor pressure sensors are arranged in the pressure-receiving range, and pressure applied thereto is detected as changes in the quantity of electricity.

Figure 34:
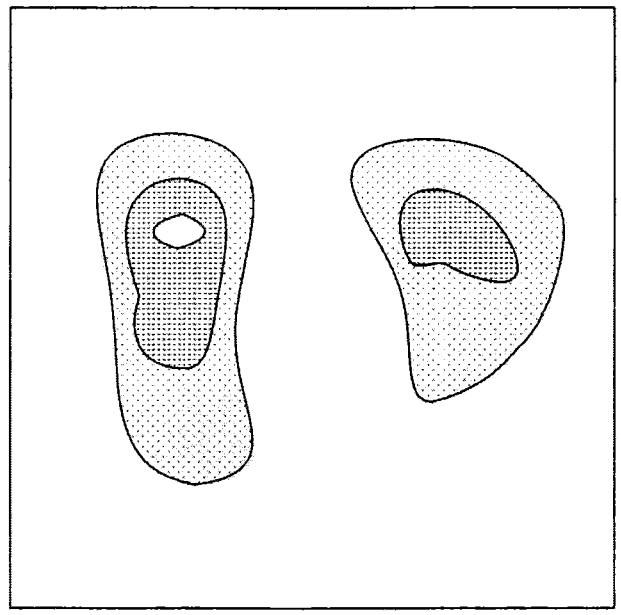
FIG. 34 is a drawing showing an operator sensor according to a seventh embodiment.
Figure 35:
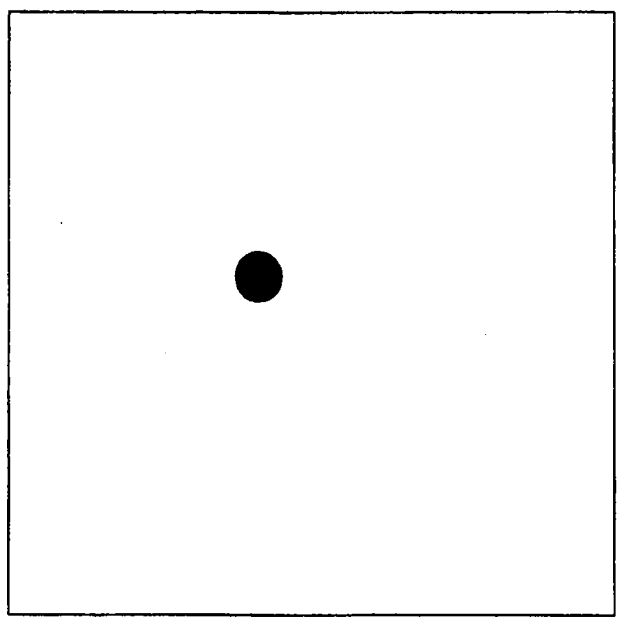
FIG. 35 is a drawing showing the barycentric position on a pressure sensor mat.

Next, further details are described with reference to FIG. 34 and FIG. 35. FIG. 34 shows a pressure distribution pattern image of the entirety of both feet. The pixels forming the pressure distribution pattern image shown in FIG. 34 have pressure values. The pressure distribution pattern of the left foot has 3 constant-pressure lines connecting pixels with the same pressure values, while the pressure distribution pattern of the right foot has 2 constant-pressure lines, showing that the operator is applying their weight on their left foot. Based on the barycenter of the pressure values related to the left foot obtained based on the pressure values of the pixels in the pressure distribution pattern of the left foot, and on the barycenter of the pressure values related to the right foot obtained based on the pressure values of the pixels in the pressure distribution pattern of the right foot, the barycenter of the pressure values of the image in the pressure distribution pattern of the entirety of both feet (i.e., the barycenter of the operator) is obtained. FIG. 35 indicates the position of the obtained barycenter of the pressure values (i.e., the barycenter of the operator) with a black circle.

For example, for multiple barycentric positions collected in the past 3 seconds, a statistical process is performed and variations (standard deviation) are obtained. When the standard deviation is greater, it may be deduced that larger body motion has occurred. Consequently, the importance-level determination part 27 deduces the importance level of the X-ray image in response to the standard deviation of the barycentric position of the operator. This is because it is deduced that the importance levels of the X-ray images are high when the operator does not perform large body motions (e.g., the operator moving by lowering their upper body forward or sideways).

Eighth Embodiment

The detector 33 according to the third through seventh embodiments described above detects the posture of the operator as the working state of the operator. This is because the working state of the operator during catheterization under X-ray fluoroscopy reveals itself in the posture of the operator manipulating the wire while viewing the display. The working state of the operator during catheterization under X-ray fluoroscopy also reveals itself as biological information indicating a tense state, such as the restraining of respiration during wire manipulation. Consequently, the detector 33 may detect biological information as the working state of the operator. Here, biological information refers to information regarding movement, etc. that occurs in a living body based on stimulation.

An example is described in which the detector 33 detects biological information of the operator as the working state of the operator. In catheterization under X-ray fluoroscopy, if the operator restrains their respiration, it is deduced that the operator is performing precise manipulations of the wire and that the importance level of the X-ray image acquired at that time is therefore high. Therefore, the state of restraint of respiration of the operator is used as biological information.

As one example of the detector 33, a stethoscopic microphone (skin-contact microphone) is attached to the operator, and collects and records heartbeat data. Moreover, as another example of the detector 33, an ECG telemeter may be attached to the operator and configured to wirelessly collect and record an electrocardiogram.

Figure 36:
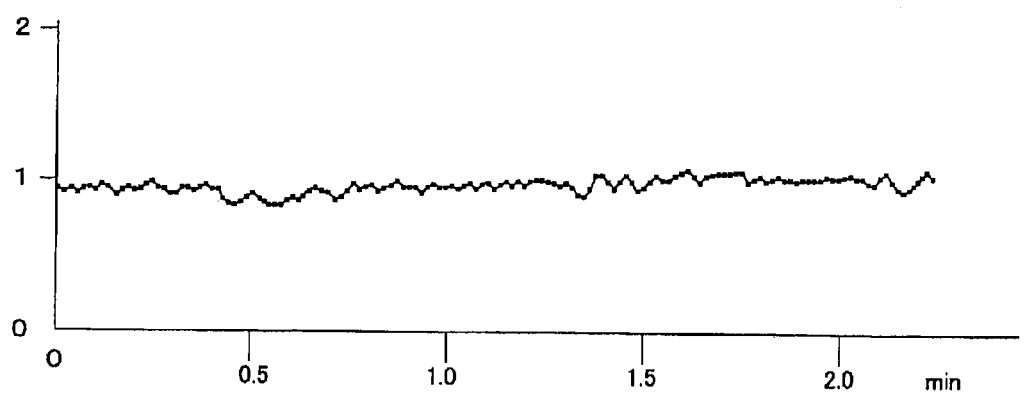
FIG. 36 is a diagram showing the heart rate of the operator when a wire is not being manipulated in an eighth embodiment.
Figure 37:
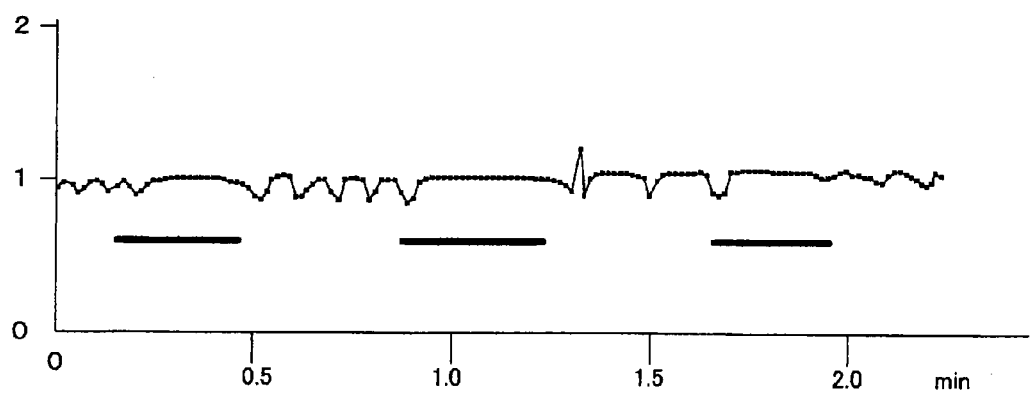
FIG. 37 is a diagram showing the heart rate of the operator when a wire is being manipulated.

The relationship between respiration and heart rate will be described further with reference to FIG. 36 and FIG. 37, in which the vertical axis is the cardiac cycle and the horizontal axis is the time axis. FIG. 36 shows a cardiac cycle during normal respiration, and the cardiac cycle changes in all time periods and there are no time periods in which the cardiac cycle becomes almost constant. FIG. 37 shows a cardiac cycle when respiration is restrained, and there is a time period (the underlined part) where the heart rate becomes almost constant and a time period where the cardiac cycle does not become almost constant.

The fact that the heart rate changes due to respiration is well known. It is likely that for any operator, it is necessary to breathe shallowly or stop breathing (i.e., restrain respiration) when performing precise manipulations. In other words, if the state in which respiration is restrained (the state indicated by the underline in FIG. 37) lasts for a long time period, this is a likely candidate for the performance of precise operations. When respiration is restrained, the heart rate becomes almost constant.

Therefore, the detector 33 detects fluctuations (standard deviation) in the heart rate of the operator during a predefined time that has passed (e.g., the past 10 seconds). The importance-level determination part 27 deduces the importance level of the X-ray image in response to the standard deviation of the heart rate. This is because it is deduced that the importance levels of the X-ray images are high when the operator is performing precise manipulations.
(Variation)

In the eighth embodiment, an example was described in which the results of detecting whether or not the operator has restrained their respiration are used as biological information of the operator. However, in catheterization under X-ray fluoroscopy, when the operator manipulates the wire, because very precise manipulations are required of the operator when the operator manipulates the wire, the operator enters a tense state and the effects thereof are revealed in the biological information of the operator. The tense state of the operator is related to the importance levels of the X-ray images acquired under that state. Consequently, the results of detecting biological information of the operator revealing the effects of a tense state may be used as the biological information of the operator detected by the detector 33. Examples of biological information of the operator revealing the effects of a tense state include the results of detecting whether or not the operator is in a tense state by detecting the brain waves, pupil diameter, frequency of blinking, degree of perspiration in the skin of the palms or the soles of the feet, or skin temperature of the operator. It should be noted that the reason for detecting the degree of perspiration in the skin of the palms or the soles of the feet is that there are high numbers of sweat glands in the palms and the soles of the feet that perspire during a tense state.

A variation of the eighth embodiment described above will now be described. In the present variation, an example is described in which the brain waves of the operator are used as biological information of the operator. The main types of brain waves are a waves, β waves, and ∝ waves, and the brain waves become β waves with a frequency of 13 Hz or more in a tense state, and become α waves with a frequency of less than 13 Hz as a state of relaxation is entered. Consequently, it is possible to detect the brain waves of the operator using the detector 33 and to use the detected results as information for determining whether or not the operator is in a tense state.

The detector 33 is worn by the operator and detects the brain waves of the operator, and the importance-level determination part 27 deduces the importance levels of the X-ray images in response to the results of detecting the brain waves of the operator. This is because it is deduced that the importance levels of the X-ray images acquired at the time are high when the operator is, for example, manipulating a wire and is in a tense state.

Next, another variation is described in which the degree of perspiration in the skin of the palms or the soles of the feet of the operator is used. As described above, when the operator is in a tense state, the amount of sweat generated from the skin of the palms or the soles of the feet of the operator increases. Therefore, the detector 33 that detects perspiration is attached to the operator, and the degree of perspiration occurring from the palms, etc. is detected at a prescribed time interval as moisture content or electric potential. Examples of the detector 33 that detects the degree of perspiration include that disclosed in Japanese published unexamined application Hei 7-143968.

Consequently, the importance-level determination part 27 deduces the importance levels of the X-ray images in response to the results detected by the detector 33. This is because it is deduced that the importance levels of the X-ray images is high when the operator is, for example, manipulating a wire and is in a tense state.

In the above variations, when detecting the biological information of the operator, the detector 33 attached to the operator is used, but a variation using the detector 33 not attached to the operator will now be described. In this variation, the pupil diameter of the operator is used as the biological information of the operator. It is known that the pupil diameter becomes greater during a tense state compared to a relaxed state. Consequently, the importance levels of the X-ray images are deduced in response to the size of the pupil diameter of the operator. This is because it is deduced that the importance levels of the X-ray images are high when the operator is, for example, manipulating a wire and is in a tense state.

Examples of the detector 33 that detects the pupil diameter of the operator include that disclosed in Japanese published unexamined application Hei 10-262953. The detector 33 includes, for example, a camera attached on or near a display. Using the camera, a facial image of the operator is acquired at a prescribed time interval, and the acquired facial image of the operator is image processed to extract the shape of the pupils. It is possible to detect the pupil diameter from the extracted shape of the pupils.

The importance-level determination part 27 deduces the importance levels of the X-ray images in response to the size of the pupil diameter. This is because it is deduced that the importance levels of the X-ray images acquired at the time are high when the operator is, for example, manipulating a wire and is in a tense state.

Next, another variation using the detector 33 that is not attached to the operator will be described. In this variation, blinks of the operator are used as the biological information of the operator. Generally, the frequency of blinking is normally 15 to 20 times per minute (the cycle between each blink is 3 to 4 seconds). The cycle of blinks decreases when viewing something with concentration. Because the operator should carefully view the display during wire manipulation requiring precise operations, the cycle of blinks should become longer.

Examples of the detector 33 that detects the blinks of the operator include that disclosed in Japanese published unexamined application 2003-338952. The detector 33 includes, for example, a camera attached on or near a display. The detector 33 continuously monitors the region of the eyes of the operator, and detects blinks based on whether or not the pupil becomes smaller. The detector 33 detects the time from the detection of one blink to the detection of the following blink (i.e., the cycle of blinks).

Consequently, the importance-level determination part 27 deduces the importance levels of the X-ray images in response to the cycle between each blink. This is because it is deduced that the importance levels of the X-ray images acquired at the time is high when the cycle between blinks is long and the operator is viewing the display with concentration.

Ninth Embodiment

Another embodiment of the present invention will now be described. An example is described in which the detector 33 detects the behavior of the operator as the working state of the operator. Here, the behavior of the operator includes the frequency of conversation between the operator and staff at a medical site and the amount of motion of the operator. During catheterization under X-ray fluoroscopy, if the frequency of conversation between the operator and staff is high, or if the amount of motion of the operator is high, it is deduced that precise manipulations of the wire are not being performed and that the importance levels of the X-ray images acquired at such times is low.

First, as the detector 33 that detects the frequency of conversation, the contact microphone described in Japanese published unexamined application 2010-5326, for example, is used. Using this microphone that is worn by the operator, the loudness of sounds (decibels (dB)) is detected instead of audio. If, for example, the mean value of the loudness of sounds over the past 3 seconds exceeds a threshold value, the importance-level determination part 27 deems that a conversation has occurred, obtains the ratio of the time spent on conversation within the past 20 seconds, and deduces the importance levels of the X-ray images in response to the obtained ratio of time spent on conversation. Furthermore, it is also possible to simply deduce the importance levels of the X-ray images in response to the mean value of the loudness of sounds over the past 3 seconds, for example. Moreover, the detector 33 that detects the frequency of conversation is not limited to a contact microphone, and a microphone that collects sounds from the operator and his/her surroundings may be used. If multiple microphones with directivity are arranged facing the operator and the multiple microphones collect sound, the collected sound is deemed to be sounds from the operator and their surroundings, and it is deduced that the operator is engaged in a conversation.

Furthermore, instead of these types of microphones, the detector 33 that detects the frequency of conversation may be an ECG telemeter. In other words, using an ECG telemeter attached to the operator, variations in the heart rate are detected, and when the heartbeats become noncyclical, it is deemed that irregular respiration is occurring and that a conversation is taking place. The detector 33 detects the frequency spectrum of chronological changes in the cardiac cycle of the operator over a predefined time in the past (e.g., the past 20 seconds). The importance-level determination part 27 deduces the importance levels of the X-ray images in response to spectral components generated by normal respiration. This is because it is deduced that the frequency of conversation is high, that the operator is not performing wire manipulations, and that the importance levels of the X-ray images acquired at the time is low.

Next, for the detector 33 that detects motions of the operator, and example using the medical-site display system described in the above Japanese published unexamined application 2010-5326 is described. To briefly describe this system, an imaging device is placed in a medical site and captures video of the medical site. Moreover, RF tags are attached to staff, including the operator, and transmit staff identification information. A receiving device is provided in the medical site. Using this, it is possible to not only record the medical site as footage but also to identify staff and their present positions and to identify and display the staff in the medical site in the recorded footage. By using this system, it is possible to easily and chronologically detect whether or not the operator has entered the frontal region (i.e., a region to which the screen is faced, that is within a specific distance from the screen) of the screen of the display, as well as how the operator is moving within the frontal region.

The importance-level determination part 27 deduces the importance levels of the X-ray images in response to the results of detecting the frequency of motion of the operator within the frontal region. This is because it is deduced that the frequency of motion of the operator is high, that wire manipulations are not being performed, and that the importance levels of the X-ray images acquired at the time is low.

Furthermore, if the operator does not enter the frontal region, or if the operator exits the frontal region, the importance-level determination part 27 deduces that the importance level of the X-ray images is low. This is because it is deduced that the operator has become very distant from the display and that the importance levels of the X-ray images acquired at the time are therefore low.

Next, for the detector 33 that detects motions of the operator, a position encoder of the bed or the X-ray gantry may be used. If the operator is manipulating the bed or the X-ray gantry (the angle of the C-arm, etc.), the importance-level determination part 27 deduces that the importance levels of the X-ray images are low. This is because the operator is not performing wire manipulations when they are manipulating the bed, etc., and it is therefore deduced that the importance levels of the X-ray images acquired at the time are low.

The above has included descriptions of the detector 33 that detects any one of the manipulated state of the wire being manipulated by the operator, the posture of the operator, the biological information of the operator, or the behavior of the operator and outputs those as detection results of the working state of the operator, as well as the importance-level determination part 27 that deduces the importance levels of the X-ray images in response to those detection results.

Tenth Embodiment

Next, a system equipped with multiple detectors 33 will be described. In this case, based on the output from the multiple detectors 33, it is necessary to deduce the importance levels of the X-ray images, synthesize these importance levels, and determine the comprehensive importance levels of the X-ray images. When determining the comprehensive importance levels of the X-ray images, for example, importance levels of X-ray images deduced based on, for example, the manipulated state of the instrument (wire) handled by the operator should be prioritized in relation to importance levels of X-ray images deduced based on the posture of the operator, the biological information of the operator, and the behavior of the operator.

Such techniques for combining information (the deduced importance levels) of differing levels of reliability are known, and for example, fuzzy logic may be used. In other words, a measure expressing the "importance level of an X-ray image" is calculated as a membership function of the fuzzy logic, and a suitable X-ray dosage is determined based thereon.

In the above, an example has been described in which, in a system equipped with multiple detectors 33, fuzzy logic is used to synthesize importance levels deduced from the output results from the multiple detectors 33 and determine the comprehensive importance levels of the X-ray images, but it is also possible to assign a weight to the deduced importance levels according to each detector 33, and to determine the comprehensive importance levels based on the results after weighting.

Moreover, even for identical operations, each operator has their own characteristics. Because those characteristics of the operator reveal themselves in the output results of the detectors 33, a weighting database that stores combinations of weights for the output results of the detectors 33 for each operator may be provided. When determining the comprehensive importance levels of the X-ray images, the importance-level determination part 27 reflects the combinations of weights corresponding to the operator in the detection results of the multiple detectors 33.

The selection means of the X-ray medical imaging apparatus simply needs to deduce the respective importance levels of X-ray images based on data representing multiple working states of different types, and determine the comprehensive importance level by synthesizing (combining and accumulating) each deduced importance level, and the combinations of each importance level described in the above embodiments are nothing more than examples.

For example, in the first embodiment, the importance-level determination part 27 deduces importance levels by using the acquisition period of the X-ray images as information for making a determination. This deduces that the importance level of an X-ray image for which the elapsed time at which the X-ray image was acquired is an early stage is low, but that deduction is not necessarily accurate, and X-ray images acquired in the beginning may have high importance levels. If the operator remembers this, a more accurate determination may be made by determining the comprehensive information levels without using the acquisition period of the X-ray images as information for making a determination. Therefore, a configuration may be used in which, when synthesizing (combining) each deduced importance level, an instruction is received from the operating part 32, the selection part 26 selects the importance levels to combine, and importance levels that may reduce the accuracy of the comprehensive importance levels are not selected. Moreover, regarding importance levels that may reduce the accuracy of the comprehensive importance levels, the importance-level determination part 27 may deduce that the importance levels are constant.

In the above embodiments, images of high importance are selected from among X-ray moving images captured by the medical imaging apparatus and are displayed in a list as thumbnails, but the present invention is not limited to this. Other modalities (e.g., a magnetic resonance diagnosis apparatus or an ultrasound diagnosis apparatus, etc.) may be used to capture moving images related to a subject, select images of high importance from among the moving images, and display the selected images in a list as thumbnails. The present invention may thus be applied generally to medical image diagnosis apparatuses.

Explanation of the Symbols

1: Subject
2: Top board
4: X-ray tube
6: X-ray detector
20: Arithmetic and control unit
21: System controller
22: Memory
23: Image processor
24: Display controller
25: X-ray dosage determination part
26: Selection part
27: Importance-level determination part
31: Display
32: Operating part
33: Detector
41: Wire identifying part
43: Alignment processor

What is claimed is:

1. A medical imaging apparatus that displays X-ray moving images by irradiating a subject with X-rays and detecting X-rays that have penetrated said subject, comprising:
    a selection means that, based on working-state information related to a working state of an operator performing surgery on said subject, selects images of high importance from among said X-ray moving images; and
    a display means that displays a list of said selected images as thumbnails, wherein
    said selection means includes an importance-level determination means that obtains importance levels of the images within said X-ray moving images based on a plurality of said working-state information, and
    said importance-level determination means obtains said importance levels based on a length of time of continuous motion of a cord inserted into said subject.

2. The medical imaging apparatus according to claim 1, wherein said importance-level determination means obtains said importance levels based on a manipulated state of said cord inserted into the subject by said operator.

3. The medical imaging apparatus according to claim 1, wherein, said display means displays, together with said thumbnails, information on their respective imaging times or elapsed times from start of surgery to imaging times.

4. The medical imaging apparatus according to claim 1, wherein said importance-level determination means obtains said importance levels based on facial orientation or line of sight of said operator.

5. The medical imaging apparatus according to claim 1, wherein said importance-level determination means obtains said importance levels based on at least one of either frequency of body motion of said operator or frequency of conversation of said operator.

6. The medical imaging apparatus according to claim 1, wherein said importance-level determination means obtains said importance levels based on information on respiration of said operator.

7. The medical imaging apparatus according to claim 1, wherein said importance-level determination means obtains said importance levels based on electrocardiogram information of said operator.

8. The medical imaging apparatus according to claim 1, wherein said importance-level determination means obtains said importance levels based on X-ray dosage size when irradiating said subject with X-rays.

9. The medical imaging apparatus according to claim 1, wherein said importance-level determination means obtains said importance levels based on an amount of change in pixel values of images within said X-ray moving images.

10. The medical imaging apparatus according to claim 1, wherein said importance-level determination means obtains said importance levels based on an amount of motion of said cord inserted into said subject.

11. The medical imaging apparatus according to claim 1, wherein said importance-level determination means lowers said importance levels of images acquired at times near times at which the images selected by said selection means are acquired.

12. The medical imaging apparatus according to claim 1, wherein said selection means performs the selection of said images in descending order of the importance levels obtained by said importance-level determination means.

13. The medical imaging apparatus according to claim 1, wherein said selection means selects the image with highest said importance level from among said plurality of selected images as a representative thumbnail.

14. The medical imaging apparatus according to claim 13, further comprising an operating part, wherein
said selection means receives an instruction from the operating part, and instead of the image selected as said representative thumbnail, selects another image as a new representative thumbnail.

15. The medical imaging apparatus according to claim 1, wherein said display means associates said images with a timescale and displays said images.

16. The medical imaging apparatus according to claim 9, wherein said display means associates said images with marks indicating the importance level of the relevant image and displays said images.

17. The medical imaging apparatus according to claim 16, wherein said display means displays said marks in a mode corresponding to said importance level.

18. The medical imaging apparatus according to claim 1, further comprising a playback means that, when an image is selected from said list, plays back said X-ray moving images from a position corresponding to the selected image.

19. A medical imaging apparatus that displays X-ray moving images by irradiating a subject with X-rays and detecting X-rays that have penetrated said subject, comprising:
an importance-level determination means that determines importance levels of images of said X-ray moving images;
a selection means that, based on the importance level determined by said importance-level determination means, selects images from among said X-ray moving images; and
a display means that displays a list of said selected images as thumbnails, wherein
said importance-level determination means determines the importance levels of the images of said X-ray moving images based on a plurality of working-state information related to a working state of an operator performing surgery on said subject, and
said importance-level determination means determines the importance levels based on a length of time of continuous motion of a cord inserted into said subject.

20. A medical image diagnosis apparatus that captures X-ray moving images related to a subject, comprising:
a selection means that selects images of high importance from among said X-ray moving images; and
a display means that displays a list of said selected images as thumbnails, wherein
said selection means includes an importance-level determination means that obtains importance levels of the images within said X-ray moving images based on a plurality of working-state information related to a working state of an operator performing surgery on said subject, and
said importance-level determination means determines said importance levels based on a length of time of continuous motion of a cord inserted into said subject.

* * * * *